US012576160B2

(12) United States Patent
Nallathamby

(10) Patent No.: US 12,576,160 B2
(45) Date of Patent: Mar. 17, 2026

(54) BISPECIFIC NANOPARTICLE SYSTEMS FOR TARGETING CANCER CELLS

(71) Applicant: University of Notre Dame du Lac, South Bend, IN (US)

(72) Inventor: Prakash Daniel Nallathamby, South Bend, IN (US)

(73) Assignee: University of Notre Dame du Lac, South Bend, IN (US)

( * ) Notice: Subject to any disclaimer, the term of this patent is extended or adjusted under 35 U.S.C. 154(b) by 311 days.

(21) Appl. No.: 18/547,664

(22) PCT Filed: May 6, 2022

(86) PCT No.: PCT/US2022/028013
§ 371 (c)(1),
(2) Date: Aug. 23, 2023

(87) PCT Pub. No.: WO2022/236012
PCT Pub. Date: Nov. 10, 2022

(65) Prior Publication Data
US 2024/0148899 A1 May 9, 2024

Related U.S. Application Data

(60) Provisional application No. 63/185,562, filed on May 7, 2021.

(51) Int. Cl.
A61K 47/69 (2017.01)
A61K 9/51 (2006.01)
(Continued)

(52) U.S. Cl.
CPC ........ A61K 47/6929 (2017.08); A61K 9/5192 (2013.01); A61K 40/11 (2025.01);
(Continued)

(58) Field of Classification Search
CPC ................................................. A61K 47/6929
See application file for complete search history.

(56) References Cited

U.S. PATENT DOCUMENTS

| | | |
|---|---|---|
| 9,249,217 B2 | 2/2016 | Bigner et al. |
| 2020/0172629 A1 | 6/2020 | Azab et al. |
| 2020/0405640 A1 | 12/2020 | Zhang et al. |

FOREIGN PATENT DOCUMENTS

| | | | | |
|---|---|---|---|---|
| CN | 105435226 A | * | 3/2016 | ......... A61K 41/0052 |
| RU | 2729617 C1 | | 8/2020 | |

(Continued)

OTHER PUBLICATIONS

Teemu T. Junttila et al. "Antitumor Efficacy of a Bispecific Antibody That Targets HER2 and Activates T Cells." Cancer Research, vol. 74(19), Oct. 1, 2014, pp. 5561-5571. (Year: 2014).*
(Continued)

*Primary Examiner* — Isaac Shomer
(74) *Attorney, Agent, or Firm* — Michael Best & Friedrich LLP

(57) ABSTRACT

Described herein are compositions and methods for targeting cancer cells and inducing cell death. In one embodiment, the composition comprises a nanoparticle system comprising a plurality of antibodies that recognize CAR-T cells and a plurality of antibodies that recognize cancer cells. The composition targets CAR-T cells to the vicinity of cancer cells, whereby upon activation, the CAR-T cells can effectuate cancer cell death.

12 Claims, 18 Drawing Sheets
Specification includes a Sequence Listing.

Tumor Cell Surface

(51) Int. Cl.

| | |
|---|---|
| *A61K 39/00* | (2006.01) |
| *A61K 40/11* | (2025.01) |
| *A61K 40/24* | (2025.01) |
| *A61K 40/31* | (2025.01) |
| *A61K 40/42* | (2025.01) |
| *A61K 47/68* | (2017.01) |
| *A61P 35/00* | (2006.01) |

(52) U.S. Cl.
CPC .............. *A61K 40/24* (2025.01); *A61K 40/31* (2025.01); *A61K 40/421* (2025.01); *A61K 47/6855* (2017.08); *A61K 47/6923* (2017.08); *A61P 35/00* (2018.01); *A61K 2039/505* (2013.01)

(56) References Cited

FOREIGN PATENT DOCUMENTS

| | | | | |
|---|---|---|---|---|
| WO | WO-2018166527 A1 * | 9/2018 | ............. | A61K 39/44 |
| WO | 2020/205579 A1 | 10/2020 | | |

OTHER PUBLICATIONS

English Tnralsation of CN 105435226 A. "Anti-tumor nano composite particle and preparation method and application thereof." Obtained from https://patents.google.com/patent/CN105435226A/en?oq=CN+105435226+ on Oct. 9, 2025, originally published in 2016 in Chinese, pp. 1-8. (Year: 2016).*
Nghiem Thi Ha Lien et al. "Theranostic Gold Nanoshells: From Synthesis to Imaging and Photothermal Therapy Applications." Communications in Physics, vol. 24, No. 3S2, 2014, pp. 63-70. (Year: 2014).*
Paulina Dobrowolska et al. "Application of Turkevich Method for Gold Nanoparticles Synthesis to Fabrication of SiO2@Au and TiO2@Au Core-Shell Nanostructures." Materials, vol. 8, 2015, pp. 2849-2862. (Year: 2015).*
B.J. Jankiewicz, D. Jamiola, J. Choma, and M. Jaroniec. "Silica-metal core-shell nanostructures." Advances in Colloid and Interface Science, vol. 170, 2012, pp. 28-47. (Year: 2012).*
English Translation of WO 2018166527 A1. "Multispecific Antibody, Antibody Conjugate and Related Pharmaceutical Composition and Use." Translation obtained Aug. 8, 2025, originally published in Chinese on Sep. 20, 2018, pp. 1-16. (Year: 2018).*
European Patent Office. Extended European Search Report for Application No. 22799654.3, dated Jun. 27, 2025 (8 pages).
Gong, N., et al. "Nanomaterials for T-cell cancer immunotherapy." Nature nanotechnology 16.1 (2021): 25-36.
Song, W. et al. "Nanotherapeutics for immuno-oncology: a crossroad for new paradigms." Trends in cancer 6.4 (2020): 288-298.
International Search Report and Written Opinion for Application No. PCT/US2022/028013 dated Oct. 6, 2022 (11 pages).
Adewale et al., "Toxicological Behavior of Gold Nanoparticles on Various Models: Influence of Physicochemical Properties and Other Factors," Int. J. Toxicol., 2019, 38(5): 357-384.
Alhallak et al., "Nanoparticle T-cell engagers as a modular platform for cancer immunotherapy," Leukemia Jan. 21, 2021. doi: 10.1038/s41375-021-01127-2 (2021).

American Cancer Society, "Cancer Facts and Figures 2020" (2020), <www.cancer.org/research/cancer-facts-statistics/all-cancer-facts-figures/cancer-facts-figures-2020.html>.
Depil et al. "'Off-the-shelf' allogeneic CAR T cells: development and challenges," Nat. Rev. Drug Discov., 2020, 19: 185-199.
Feins et al., "An introduction to chimeric antigen receptor (CAR) T-cell immunotherapy for human cancer," Am. J. Hematol., 2019, 94: 3-9.
Fesnak et al., "Production of Chimeric Antigen Receptor T cells," Stemcell™ Technologies (2017); < www.stemcell.com/media/files/wallchart/10000009078-Production_of_Chimeric_Antigen_Receptor_T_Cells.pdf>.
Herceptin® trastuzumab product information, 1998.
Hopf et al., "Phage-mimicking antibacterial core-shell nanoparticles," Nanoscale Adv., 2019, 1: 4812-4816.
Ilag et al., "DNA packaging intermediates of bacteriophage φ174," Structure, 1995, 3(4): 353-363.
Kuhn et al., "Therapeutic anti-CD3 monoclonal antibodies: from bench to bedside," Immunotherapy, 2016, 8(8): 889-906.
Lu et al., "Integrated metabonomics analysis of the size-response relationship of silica nanoparticles-induced toxicity in mice," Nanotechnology, 2011, 22: 055101.
Nanoprobes, <www.nanoprobes.com/products/AuroVist-Gold-X-ray-Contrast-Agent.html> webpage available as early as Oct. 7, 2013.
Nebuloni et al., "A Comparative Analysis of Water-Soluble and Blood-Pool Contrast Agents for in vivo Vascular Imaging with Micro-CT," Academic Radiology, 2013, 20(10): 1247-1255.
Nghiem et al., "Preparation and characterization of silica-gold core-shell nanoparticles," J. Nanopart. Res., 2013, 15: 2091.
Rafiq et al., "Engineering strategies to overcome the current roadblocks in CAR T cell therapy," Nat. Rev. Clin. Oncol., 2020, 17: 147-167.
Shalabi et al., "Beyond the storm—subacute toxicitéceiving CAR T cells," Nature Reviews Clinical Oncology, 2021, 18: 363-378.
Shi et al., Genetically Engineered Cell-Derived Nanoparticles for Targeted Breast Cancer Immunotherapy, Molecular Therapy, 2020, 28(2): 536-547.
Stöber et al., "Controlled growth of monodisperse silica spheres in the micron size range," J. Colloid Interface Sci. 26(1): 62-69 (1968).
Urba et al., "Anti-CD Monoclonal Antibody Treatment of Patients with CD3-Negative Tumors: A Phase IA/B Study," Cancer Res., 1992, 52: 2394-2401.
Wang et al., "Volume labeling with Alexa Fluor dyes and surface functionalization of highly sensitive fluorescent silica (SiO2) nanoparticles," Nanoscale, 2013, 5: 10369-10375.
Wiczling et al., "Pharmacokinetics and pharmacodynamics of a chimeric/humanized anti-CD3 monoclonal antibody, otelixizumab (TRX4), in subjects with psoriasis and with type 1 diabetes mellitus," J. Clin. Pharmacol., 2010, 50(5): 494-506.
Yu et al., "A novel asymmetrical anti-HER2/CD3 bispecific antibody exhibits potent cytotoxicity for HER2-positive tumor cells," J. Exp. Clin. Cancer Res., 2019, 38: 355.
Yu et al., "In Vivo Biodistribution and Pharmacokinetics of Silica Nanoparticles as a Function of Geometry, Porosity and Surface Characteristics," J. Control. Release, 2012, 163(1): 46-54.
Zhang et al., "CAR-T Cell Therapy in Cancer: Tribulations and Road Ahead," J. Immunol. Res., 2020: 1924379 (2020).

* cited by examiner

Tumor Cell Surface

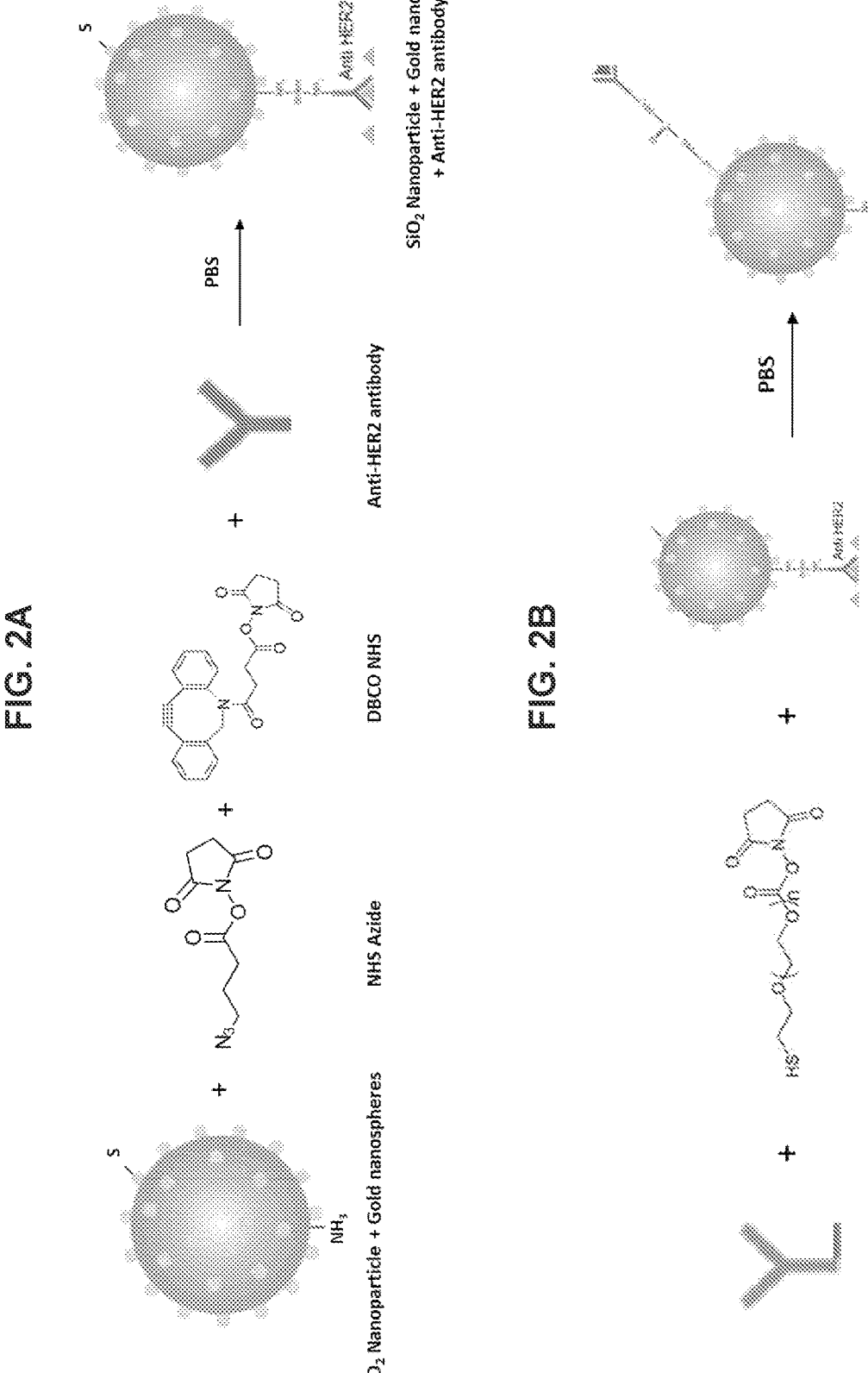

SKBR3-Breast
Cancer

SKOV3-Ovarian
Cancer

PC3-Prostate
Cancer

HUVEC-
Endothelial Cells

Nanoparticles + Cells

Cells Only

| SKBR3-Breast Cancer | SKOV3-Ovarian Cancer | PC3-Prostate Cancer | HUVEC- Endothelial Cells |
|---|---|---|---|
Nanoparticles + uCAR-T Cells
| FIG. 5A | FIG. 5B | FIG. 5C | FIG. 5D |
|---|---|---|---|
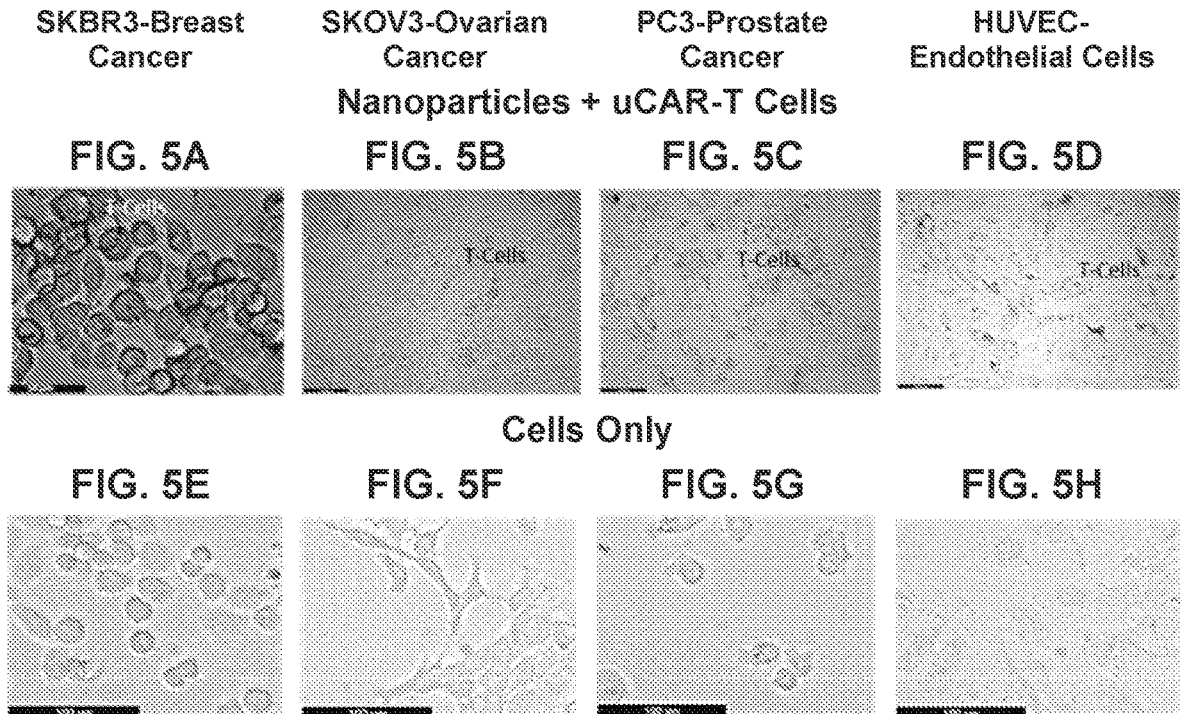
Cells Only
| FIG. 5E | FIG. 5F | FIG. 5G | FIG. 5H |
|---|---|---|---|

SKBR3-Breast
Cancer

SKOV3-Ovarian
Cancer

PC3-Prostate
Cancer

HUVEC-
Endothelial Cells

Nanoparticles + uCAR-T CD-19 Cells

Nanoparticles + Control Cells

SKBR3-Breast
Cancer

SKOV3-Ovarian
Cancer

PC3-Prostate
Cancer

HUVEC-
Endothelial Cells

Nanoparticles + uCAR-T CD-19 Cells

Nanoparticles + Control Cells

Total Non Apoptotic Cells

Total Live Cells

Total Viable Cells

Kidney      Spleen      Heart

Liver      Lung      Brain

Kidney      Spleen      Heart

Liver      Lung      Brain

BISPECIFIC NANOPARTICLE SYSTEMS FOR TARGETING CANCER CELLS

CROSS-REFERENCE TO RELATED APPLICATIONS

This application is a U.S. national stage entry of International Patent Application No. PCT/US2022/028013, filed on May 6, 2022, which claims priority to U.S. Provisional Patent Application No. 63/185,562, filed on May 7, 2021, the entire contents of each of which are fully incorporated herein by reference.

REFERENCE TO SEQUENCE LISTING

This application was filed with a Computer Readable Form of a Sequence Listing in ST.25 format in accordance with 37 C.F.R. § 1.831. The Sequence Listing ST.25 text file submitted in the USPTO Patent Center, "092012-9144-US02_sequence_listing_8 Jan. 2026_ST25.txt," was created on Jan. 8, 2026, contains 1 sequence, has a file size of 619 bytes, and is incorporated by reference in its entirety into the specification.

TECHNICAL FIELD

Described herein are compositions and methods for targeting cancer cells and inducing cell death. In one embodiment, the composition comprises a nanoparticle system comprising a plurality of antibodies that recognize CAR-T cells and a plurality of antibodies that recognize cancer cells. The composition targets CAR-T cells to the vicinity of cancer cells, whereby upon activation, the CAR-T cells can effectuate cancer cell death.

BACKGROUND

In 2020, there will be an estimated 1.8 million new cancer cases diagnosed and 606,520 cancer deaths in the United States alone [1]. The growth and advancement of immunotherapy, a treatment that helps the immune system fight cancer, has shown to be promising. One of the main challenges faced by cancer immunotherapy is tolerance to "self-antigens" where T-cell receptors (TCRs) have a low affinity to self-tumor antigens. In order to circumvent this issue, T-cells can be "reprogramed" with chimeric antigen receptors (CARs). CARs effectively link T-cell activating functions and the ability to recognize specific surface tumor antigens. It is made up of two domains. An intracellular signaling domain, TCR CD3ζ, is responsible for T-cell activation while the extracellular antigen-binding domain consists of a variable heavy and variable light chains of monoclonal antibodies. Both domains are connected by a flexible hinge forming a single chain variable fragment (scFv) portion of a CAR. The scFv has the ability to recognize and bind cell surface proteins with a very high affinity for the targeted proteins (several orders of magnitude higher than TCRs) [2]. This makes it independent of antigen processing and presentation.

In order to produce CAR-T cells, T-cells first need to be collected from the patient by leukapheresis. Once isolated, the T-cells are genetically engineered using electroporation or CRISPR CAS systems to express CARs and are then expanded and harvested ex vivo [2]. The modified T-cells are then infused back into the patient.

CAR-T therapy has shown significant success in treating hematological cancers. These almost miraculous results as well as continual advancement and understanding of the therapy has warranted recent FDA approval of CAR-T cells directed against the CD19 protein for the treatment of acute lymphocytic (or lymphoblastic) leukemia (ALL) and diffuse large B-cell lymphoma (DLBCL) [2]. However, this success is somewhat more limited in its treatment for solid tumors, which collectively account for ~90% of cancer-related deaths [3]. The disappointing results in patients with solid tumors can be attributed to several factors: (1) lack of proper targets and heterogeneity, (2) CAR-T cells are not effectively infiltrating into tumor tissue, and (3) effect of tumor microenvironment on CAR-T cell therapy [4]. CAR-T therapy has also shown to produce devastating side effects such as cytokine release syndrome and off-tumor toxicity leading to neurological symptoms. These can become severe and life-threatening if not treated correctly.

CAR-T cell therapy has proven to be very promising from results from studies in its high survival and recovery rates to cancers in stages that were previously considered incurable. However, several disadvantages of the treatment limit its efficacy though these can be improved. Currently, CAR-T cell therapy is only approved and is effective in treating hematological cancers. No significant success is shown for its treatment in solid tumors, which collectively account for about 90% of cancer-related deaths [3]. The therapy is also highly personalized in that T cells must be harvested directly from the recipient patient in order for CAR-T cells to be made. This leads to difficulties due to health risks as patients are usually lymphopenic from chemotherapy and they may have disease-related dysfunctions of T-cells, such as patients who have CLL or solid tumors. The apheresis samples collected also have a high chance of containing tumor cells, which hamper efficient CAR-T cell expansion in culture. Resistance to CAR therapy has also been attributed to failure of engraftment and/or expansion and persistence of engineered T cells [2]. The process in collecting, preserving, manufacturing, and testing the CAR-T cells is difficult and requires much time. Once the apheresis is collected by leukapheresis, it is preserved and shipped to a manufacturing site usually taking about 1 days. The apheresis is then washed and separated to select the T-cells. T-cells are then genetically modified, activated, and expanded ex vivo, which takes about 11 days. The CAR-T cells then undergo quality assessment with various tests ensuring its identity, purity, sterility, safety, and potency [5]. This step can take up to 9 days. The CAR-T cells are then shipped back to the treatment site requiring another day. This process totals to about 22 days in which patients must wait for CAR-T cells; a very large amount of time in which a cancer can significantly worsen and become fatal.

One way in which the issues of inadequate cell numbers and manufacturing time can almost be eliminated entirely is by using allogeneic T-cells. This utilizes healthy T-cells from third-party donors which are brought through the same process to produce universal CAR-T cells (uCAR-T). Allogeneic T-cells do have the possibility of mediating graft-versus-host disease (GVHD). However, recent research in the use of transcription activator-like effector nuclease (TALEN) gene-editing technology to disrupt the TCRa constant (TRAC) gene, which is responsible for GVHD, eliminates this disadvantage [6]. Allowing to collect and manufacture healthy allogeneic T-cells in essence provides "off-the-shelf" uCAR-T cells which can be stored for use in liquid nitrogen for patients to use instead of waiting 22 days for the manufacturing of their own T-cells. However, these CAR-T cells still need to be prepared for specific tumors, meaning large supplies of multiple different types of CAR-T cells that treat various types of cancers must be kept at hand requiring unnecessary resources and time.

What is needed are compositions and methods for targeting any CAR-T cell to specific tumor types for the induction of tumor cell death.

SUMMARY

One embodiment described herein is a therapeutic composition comprising: a nanoparticle system comprising a silicon dioxide core comprising on the surface a plurality of gold nanospheres conjugated to one or more tumor cell targeting domains and one or more T-cell targeting domains. In one aspect, the one or more tumor cell targeting domains comprise one or more tumor cell targeting antibodies. In another aspect, the tumor cell targeting antibodies bind HER2. In another aspect, the one or more T-cell targeting domains comprise one or more T-cell targeting antibodies. In another aspect, the T-cell targeting antibodies bind CD3. In another aspect, the one or more tumor cell targeting domains are conjugated to the silicon dioxide core. In another aspect, the one or more T-cell targeting domains are conjugated to the plurality of nanospheres. In another aspect, the nanosphere is gold, silver, copper, metal oxides, titanium oxide, iron oxide, zinc oxide. In one aspect, the nanospheres are gold nanospheres. In another aspect, the tumor cell is from breast, ovarian, or prostate tissue. In another aspect, the T-cell is a CAR-T cell. In another aspect, the silicon dioxide core comprises a mean particle diameter ranging from about 20 nm to about 200 nm. In another aspect, the silicon dioxide core comprises a mean particle diameter ranging from about 40 nm to about 150 nm. In another aspect, the plurality of gold nanospheres comprises about 50 gold nanospheres to about 100 gold nanospheres.

Another embodiment described herein is a method for targeting a T-cell to the vicinity of a tumor cell, the method comprising: contacting a surface of a T-cell and a surface of a tumor cell with a nanoparticle system comprising a silicon dioxide core comprising on the surface a plurality of gold nanospheres conjugated to one or more tumor cell targeting domains and one or more T-cell targeting domains. In one aspect, the one or more tumor cell targeting domains comprise one or more tumor cell targeting antibodies. In another aspect, the tumor cell targeting antibodies bind HER2 on the surface of the tumor cell. In another aspect, the one or more T-cell targeting domains comprise one or more T-cell targeting antibodies. In another aspect, the T-cell targeting antibodies bind CD3 on the surface of the T-cell. In another aspect, the tumor cell is from breast, ovarian, or prostate tissue. In another aspect, the T-cell is a CAR-T cell. In another aspect, the method induces tumor cell death.

Another embodiment described herein is a method for inducing tumor cell death in a subject, the method comprising: administering a therapeutically effective amount of a nanoparticle system comprising a silicon dioxide core comprising on the surface a plurality of gold nanospheres conjugated to one or more tumor cell targeting domains and one or more T-cell targeting domains, wherein the nanoparticle system targets a T-cell to the vicinity of a tumor cell and increases T-cell-mediated death of the tumor cell relative to a subject who has not been administered the nanoparticle system. In another aspect, the one or more tumor cell targeting domains comprise one or more tumor cell targeting antibodies. In another aspect, the tumor cell targeting antibodies bind HER2 on the surface of the tumor cell in the subject. In another aspect, the one or more T-cell targeting domains comprise one or more T-cell targeting antibodies. In another aspect, the T-cell targeting antibodies bind CD3 on the surface of the T-cell in the subject. In another aspect, the subject has breast cancer, ovarian cancer, prostate cancer, or another cancer with high expression of HER2. In another aspect, the T-cell is a CAR-T cell.

Another embodiment described herein is a process for manufacturing a nanoparticle system comprising a silicon dioxide core comprising on the surface a plurality of gold nanospheres conjugated to one or more tumor cell targeting domains and one or more T-cell targeting domains, the process comprising: (a) synthesizing the silicon dioxide core; (b) synthesizing the plurality of gold nanospheres; (c) immobilizing the plurality of gold nanospheres to the surface of the silicon dioxide core; (d) conjugating the one or more tumor cell targeting domains to the surface of the silicon dioxide core; and (e) conjugating the one or more T-cell targeting domains to the plurality of gold nanospheres. In one aspect, the silicon dioxide core is synthesized by performing a sol-gel method. In another aspect, the plurality of gold nanospheres is synthesized by performing alkaline reduction at room temperature. In another aspect, the one or more tumor cell targeting domains comprise one or more tumor cell targeting antibodies that binds HER2. In another aspect, the one or more T-cell targeting domains comprise one or more T-cell targeting antibodies that bind CD3. In another aspect, the silicon dioxide core comprises a mean particle diameter ranging from about 20 nm to about 200 nm. In another aspect, the silicon dioxide core comprises a mean particle diameter ranging from about 40 nm to about 150 nm. In another aspect, the plurality of gold nanospheres comprises about 50 gold nanospheres to about 100 gold nanospheres.

Another embodiment described herein is a nanoparticle system comprising a silicon dioxide core comprising on the surface a plurality of gold nanospheres conjugated to one or more tumor cell targeting domains and one or more T-cell targeting domains manufactured by the process described herein.

Another embodiment described herein is the use of a nanoparticle system comprising a silicon dioxide core comprising on the surface a plurality of gold nanospheres conjugated to one or more tumor cell targeting domains and one or more T-cell targeting domains for inducing tumor cell death.

DESCRIPTION OF THE DRAWINGS

FIG. 2A-B show a schematic of the workflow to create CAR-T cell capturing dual-antibody bridge nanoparticles and FIG. 2C shows a schematic of the method for targeting cancer cells. FIG. 2A shows that $SiO_2$ NP's are first paired with gold nanospheres, which project 3-5 nm off the surface of the $SiO_2$ NPs. The reactions in FIG. 2A conjugate the anti-HER2 antibody onto the silica surface. FIG. 2B shows the conjugation of the anti-CD3 antibody onto the gold nanospheres. FIG. 2C shows that when CAR-T cells are then added, which have a CD3 protein that attaches to the anti-CD3 antibody, a CD19 activator is also added, which attaches to the anti-CD19 antibody on the CAR-T cell and activates the CAR-T cell. Varying types of cancer cells that express HER2 are then added, which attach to the anti-HER2 antibody protein on the NP. When the NP-bound CAR-T cell is activated by CD19 and the cancer cell is attached to the NP, the released cytokines from the CAR-T cell will induce cell death of the cancer cell. Normal somatic cells will have limited effects from this because they do not express the HER2 protein on their cell surface and therefore will not attach to the NPs via the anti-HER2 antibody.

FIG. 3C shows several nanoparticles made using 45 nm silicon dioxide cores. FIG. 3D shows a nanoparticle made using a 130 nm silicon dioxide core. Scale bars are 20 nm.

FIG. 4A shows bridge NPs+ cells alone for SKBR3-HER2+ breast cancer cells. FIG. 4B shows bridge NPs+ cells alone for SKOV3-ovarian cancer cells. FIG. 4C shows bridge NPs+ cells alone for PC3-prostate cancer cells. FIG. 4D shows bridge NPs+ cells alone for HUVEC-control endothelial cells. FIG. 4E shows control-SKBR3-HER2+ breast cancer cells alone. FIG. 4F shows control-SKOV3-ovarian cancer cells alone. FIG. 4G shows control-PC3-prostate cancer cells alone. FIG. 4H shows control-HUVEC-control endothelial cells alone.

FIG. 5A-H show bright field microscopy images of tested cells added with bridge NPs and uCAR-T cells compared with control images of the cells alone. The bispecific bridge NPs successfully anchored the uCAR-T cells to the surface of the cancer cells. Insignificant uCAR-T cells were anchored to HUVECs. uCAR-T cells are rounded and smaller compared to the adherent cancer cells and are immuno-stained blue with blue fluorescent anti-CD3 antibody. FIG. 5A shows bridge NPs+uCAR-T for SKBR3-HER2+ breast cancer cells. FIG. 5B shows bridge NPs+uCAR-T for SKOV3-ovarian cancer cells. FIG. 5C shows bridge NPs+uCAR-T for PC3-prostate cancer cells. FIG. 5D shows bridge NPs+uCAR-T for HUVEC-control endothelial cells. FIG. 5E shows control-SKBR3-HER2+ breast cancer cells alone. FIG. 5F shows control-SKOV3-ovarian cancer cells alone. FIG. 5G shows control-PC3-prostate cancer cells alone. FIG. 5H shows control-HUVEC-control endothelial cells alone.

FIG. 6A shows bridge NPs+uCAR-T for SKBR3-HER2+ breast cancer cells. FIG. 6B shows bridge NPs+uCAR-T for SKOV3-ovarian cancer cells. FIG. 6C shows bridge NPs+uCAR-T for PC3-prostate cancer cells. FIG. 6D shows bridge NPs+uCAR-T for HUVEC-control endothelial cells. FIG. 6E shows bridge NPs+control cells for KBR3-HER2+ breast cancer cells. FIG. 6F shows bridge NPs+control cells for SKOV3-ovarian cancer cells. FIG. 6G shows bridge NPs+control cells for PC3-prostate cancer cells. FIG. 6H shows bridge NPs+control cells for HUVEC-control endothelial cells.

FIG. 7A shows bridge NPs+uCAR-T for SKBR3-HER2+ breast cancer cells. FIG. 7B shows bridge NPs+uCAR-T for SKOV3-ovarian cancer cells. FIG. 7C shows bridge NPs+uCAR-T for PC3-prostate cancer cells. FIG. 7D shows bridge NPs+uCAR-T for HUVEC-control endothelial cells. FIG. 7E shows bridge NPs+control cells for KBR3-HER2+ breast cancer cells. FIG. 7F shows bridge NPs+control cells for SKOV3-ovarian cancer cells. FIG. 7G shows bridge NPs+control cells for PC3-prostate cancer cells. FIG. 7H shows bridge NPs+control cells for HUVEC-control endothelial cells.

FIG. 8A-C: SKBR3 cells; FIG. 8D-F: SKOV3 cells; FIG. 8G-I; PC3 cells; FIG. 8J-L: HUVEC cells (control). FIGS. 8A, 8D, 8G, and 8J show immunostaining for phosphorylated BAD protein as a function of CD19 concentration. FIGS. 8B, 8E, 8H, and 8K show the number of live cells as a function of CD19 concentration. FIGS. 8C, 8F, 8I, and 8L show the total viable cells as a function of CD19 concentration. FIG. 8M shows the percentage of viable cells for each cell type as a function of CD19 concentration. Data for FIG. 8M are shown in Table 6.

FIG. 9A-C show assays using a ratio of uCAR-T cells to cancer cells of 1:1; FIG. 9D-F show assays using a ratio of cancer cells to uCAR-T cells of 2:1.

FIG. 10A shows 4-hours post injection. FIG. 10B shows 8-hours post injection. FIG. 10C shows 24-hours post injection. FIG. 10D shows 48-hours post injection.

FIG. 12A shows 4-hours post injection. FIG. 12B shows 8-hours post injection. FIG. 12C shows 24-hours post injection. FIG. 12D shows 48-hours post injection.

DETAILED DESCRIPTION

Figure 1:
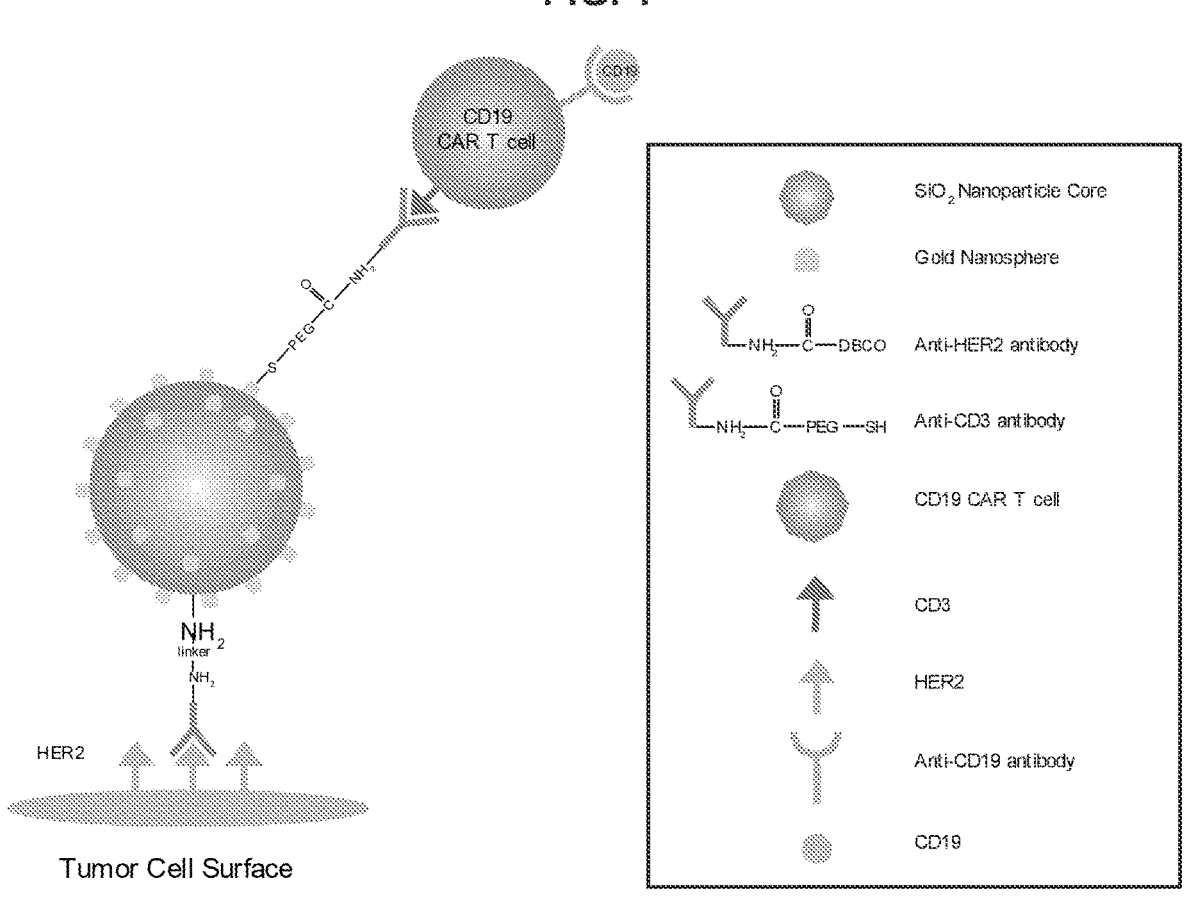
FIG. 1 shows a schematic of the universal CAR-T cell capturing dual-antibody bridge nanoparticle and the requisite components.
Figure 2C:
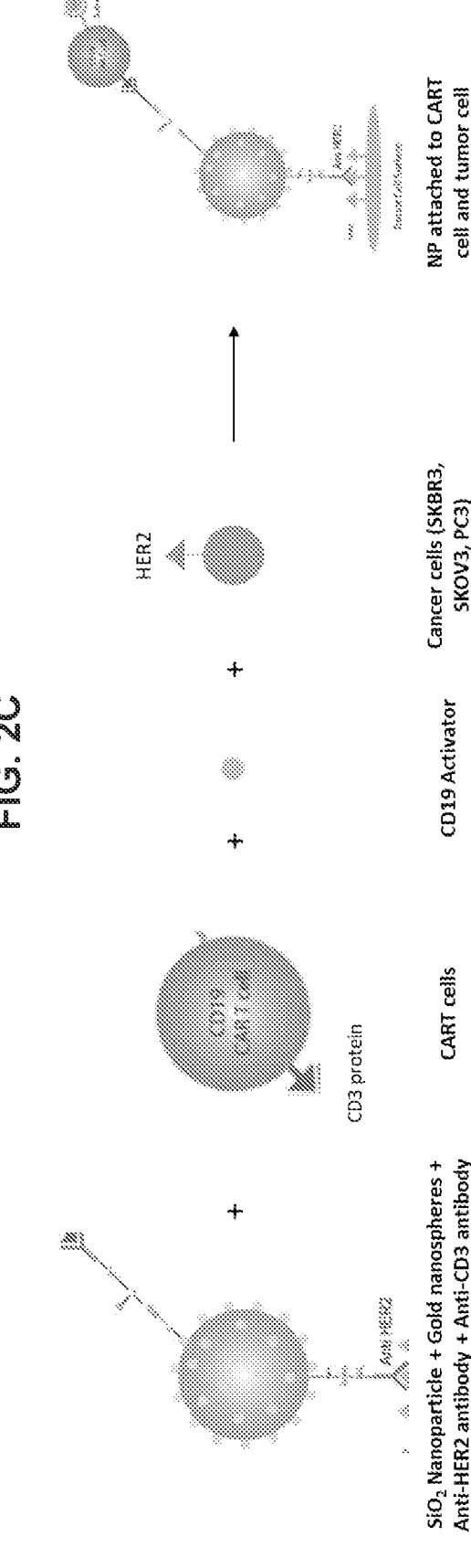

Unless otherwise defined, all technical and scientific terms used herein have the same meaning as commonly understood by one of ordinary skill in the art. For example, any nomenclatures used in connection with, and techniques of, cell and tissue culture, molecular biology, immunology, microbiology, genetics, and protein and nucleic acid chemistry and hybridization described herein are well known and commonly used in the art. In case of conflict, the present document, including definitions, will control. Representative compositions, methods, and materials are described herein, although equivalent materials and methods can be used in practice.

As used herein, the terms "amino acid," "nucleotide," "polynucleotide," "vector," "polypeptide," and "protein" have their common meanings as would be understood by a biochemist of ordinary skill in the art. Standard single letter nucleotides (A, C, G, T, U) and standard single letter amino acids (A, C, D, E, F, G, H, I, K, L, M, N, P, Q, R, S, T, V, W, or Y) are used herein.

As used herein, the terms such as "include," "including," "contain," "containing," "having," and the like mean "comprising." The present disclosure also contemplates other embodiments "comprising," "consisting of," and "consisting essentially of," the embodiments or elements presented herein, whether explicitly set forth or not.

As used herein, the term "a," "an," "the" and similar terms used in the context of the disclosure (especially in the context of the claims) are to be construed to cover both the singular and plural unless otherwise indicated herein or clearly contradicted by the context. In addition, "a," "an," or "the" means "one or more" unless otherwise specified.

As used herein, the term "or" can be conjunctive or disjunctive.

As used herein, the term "substantially" means to a great or significant extent, but not completely.

As used herein, the term "about" or "approximately" as applied to one or more values of interest, refers to a value that is similar to a stated reference value, or within an acceptable error range for the particular value as determined by one of ordinary skill in the art, which will depend in part on how the value is measured or determined, such as the limitations of the measurement system. In one aspect, the term "about" refers to any values, including both integers and fractional components that are within a variation of up to ±10% of the value modified by the term "about." Alternatively, "about" can mean within 3 or more standard deviations, per the practice in the art. Alternatively, such as with respect to biological systems or processes, the term "about" can mean within an order of magnitude, in some embodiments within 5-fold, and in some embodiments within 2-fold, of a value. As used herein, the symbol "~" means "about" or "approximately."

All ranges disclosed herein include both end points as discrete values as well as all integers and fractions specified within the range. For example, a range of 0.1-2.0 includes 0.1, 0.2, 0.3, 0.4 . . . 2.0. If the end points are modified by the term "about," the range specified is expanded by a variation of up to ±10% of any value within the range or within 3 or more standard deviations, including the end points.

As used herein, the terms "active ingredient" or "active pharmaceutical ingredient" refer to a pharmaceutical agent, active ingredient, compound, or substance, compositions, or mixtures thereof, that provide a pharmacological, often beneficial, effect.

As used herein, the terms "control," or "reference" are used herein interchangeably. A "reference" or "control" level may be a predetermined value or range, which is employed as a baseline or benchmark against which to assess a measured result. "Control" also refers to control experiments or control cells.

As used herein, the term "dose" denotes any form of an active ingredient formulation or composition, including cells, that contains an amount sufficient to initiate or produce an effect or therapeutic effect with at least one or more administrations. "Formulation" and "composition" are used interchangeably herein.

As used herein, the term "prophylaxis" refers to preventing or reducing the progression of a disorder, either to a statistically significant degree or to a degree detectable by a person of ordinary skill in the art.

As used herein, the term terms "administering" or "administration" refer to delivering a therapeutic agent as described herein to a subject and include any routes of introducing or delivering to the subject to perform the intended function. Administration can be carried out one or more suitable routes, including orally, intranasally, parenterally (intravenously, intramuscularly, intraperitoneally, or subcutaneously), intracranially, or topically. Additional routes of administration include intraorbital, infusion, intraarterial, intracapsular, intracardiac, intradermal intrapulmonary, intraspinal intrasternal, intrathecal intrauterine, intravenous, subarachnoid, subcapsular, subcutaneous, transmucosal, or transtracheal. Administration includes self-administration and the administration by another.

"Anti-cancer therapeutic" refers to any drug useful in the treatment of cancer. Various kinds of anti-cancer drugs are alkylating agents (cisplatin, chlorambucil, procarbazine, carmustine etc.), antimetabolites (methotrexate, cytarabine, gemcitabine etc.), anti-microtubule agents (vinblastine, paclitaxel etc.), topoisomerase inhibitors (etoposide, doxorubicin etc.), and cytotoxic agents (bleomycin, mitomycin etc.).

As used herein, the terms "effective amount" or "therapeutically effective amount," refers to a substantially non-toxic, but sufficient amount of an agent, composition, or cell(s) being administered to a subject that will prevent, treat, or ameliorate to some extent one or more of the symptoms of the disease or condition being experienced or that the subject is susceptible to contracting. The result can be the reduction or alleviation of the signs, symptoms, or causes of a disease, or any other desired alteration of a biological system. An effective amount may be based on factors individual to each subject, including, but not limited to, the subject's age, size, type or extent of disease, stage of the disease, route of administration, the type or extent of supplemental therapy used, ongoing disease process, and type of treatment desired.

As used herein, the term "subject" refers to an animal. Typically, the subject is a mammal. A subject also refers to primates (e.g., humans, male or female; infant, adolescent, or adult), non-human primates, rats, mice, rabbits, pigs, cows, sheep, goats, horses, dogs, cats, fish, birds, and the like. In one embodiment, the subject is a human. In another embodiment, the subject is a cell.

As used herein, a subject is "in need of treatment" if such subject would benefit biologically, medically, or in quality of life from such treatment. A subject in need of treatment does not necessarily present symptoms, particular in the case of preventative or prophylatic treatments.

As used herein, the terms "inhibit," "inhibition," or "inhibiting" refer to the reduction or suppression of a given biological process, condition, symptom, disorder, or disease, or a significant decrease in the baseline activity of a biological activity or process.

As used herein, "treatment" or "treating" refers to prophylaxis of, preventing, suppressing, repressing, reversing, alleviating, ameliorating, or inhibiting the progress of biological process including a disorder or disease, or completely eliminating a disease. A treatment may be either performed in an acute or chronic way. The term "treatment" also refers to reducing the severity of a disease or symptoms associated with such disease prior to affliction with the disease. "Repressing" or "ameliorating" a disease, disorder, or the symptoms thereof involves administering a cell, composition, or compound described herein to a subject after clinical appearance of such disease, disorder, or its symptoms. "Prophylaxis of" or "preventing" a disease, disorder, or the symptoms thereof involves administering a cell, composition, or compound described herein to a subject prior to onset of the disease, disorder, or the symptoms thereof. "Suppressing" a disease or disorder involves administering a cell, composition, or compound described herein to a subject after induction of the disease or disorder thereof but before its clinical appearance or symptoms thereof have manifest.

As used herein, the term "tumor cell targeting domains" refers to any protein or polypeptide domain that can specifically bind to a target cell or cell surface receptor. Non-limiting examples include an antibody, an antibody fragment, a single domain antibody, a bispecific antibody, a fragment of a bispecific antibody, a scFv antibody fragment, a heavy chain variable domain (VH), a light chain variable domain (VL). Non-limiting examples of the amino acid sequence and polynucleotides encoding such are provided herein. Also intended within the scope of this disclosure are biological equivalents of the exemplified polypeptide and polynucleotide sequences.

In one aspect, the T-cell targeting domain binds to an antigenic determinant or epitope on an immune cell, such as one or more of T-cells, CAR-T cells, universal CAR-T cells (uCAR-T cells), CD3+ CAR-T cells, CD3+ T-cells, NK cells, CD4+ T-cells, CD8+ T-cells, CD19+ cells, CD20+ cells, macrophages, or B cells.

As used herein, the terms "antibody," "antibodies" and "immunoglobulin" includes antibodies, antigen binding fragments, or single chains thereof. The term "antibody" includes any protein or peptide that comprises at least a portion of an immunoglobulin molecule. The terms "antibody," "antibodies," or "immunoglobulin" also include immunoglobulins of any isotype, fragments of antibodies which retain specific binding to antigen, including, but not limited to, Fab, Fab', F(ab)2, Fv, scFv, dsFv, Fd fragments, dAb, VH, VL, VhH, and V-NAR domains; minibodies, diabodies, triabodies, tetrabodies, or kappa bodies; multi-specific antibody fragments formed from antibody fragments and one or more isolated. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, at least one portion of a binding protein, chimeric antibodies, humanized antibodies, single-chain antibodies, and fusion proteins comprising, or alternatively consisting essentially of, or yet further consisting of an antigen-binding portion of an antibody and a non-antibody protein. The variable regions of the heavy and light chains of the immunoglobulin molecule contain a binding domain that interacts with an antigen. The constant regions of the antibodies may mediate the binding of the immunoglobulin to host tissues.

The antibodies can be polyclonal, monoclonal, multispecific (e.g., bispecific antibodies), or antibody fragments, as long as they exhibit the desired biological activity. Antibodies can be isolated from any suitable biological source, e.g., murine, rabbit, rat, sheep, camel, goat, or canine.

As used herein, "monoclonal antibody" refers to an antibody obtained from a substantially homogeneous antibody population. Monoclonal antibodies are highly specific, as each monoclonal antibody is directed against a single determinant on the antigen. The antibodies may be detectably labeled, e.g., with a radioisotope, an enzyme which generates a detectable product, a fluorescent protein, and the like.

As used herein, the terms "HER2" or "human epidermal growth factor receptor 2" refer to a gene that is known to play a role in the development of cancer. The HER2 gene makes HER2 proteins. HER2 proteins are receptors on cells, and particularly, breast cells. The protein coding sequence of the gene is known in the art. Antibodies and fragments to the HER2 receptor are known in the art.

As used herein, the term "SKBR3" refers to SKBR3 breast cancer cells that overexpress HER2.

As used herein, the term "SKOV3" refers to SKOV3 ovarian cancer cells that overexpress HER2.

As used herein, the term "PC3" refers to PC3 prostate cancer cells that express HER2.

As used herein, the term "HUVEC" refers to HUVEC primary endothelial cells. These cells are used as a control cell line.

As used herein, the term "uCAR-T" refers to universal CAR-T cells. Universal CAR-T cells can be any available CAR-T cells.

As used herein, the term "tumor cell targeting domain" refers to a domain of the nanoparticle that can recognize and bind to a tumor cell. In one aspect, the tumor cell is a cancer cell. In another aspect, the tumor cell targeting domain is one or more antibodies that recognize cell surface moieties on a tumor cell. In one aspect, the tumor cell targeting domain is one or more antibodies that recognize and bind to HER2 on a tumor or cancer cell.

As used herein, the term "T-cell targeting domain" refers to a domain of the nanoparticle that can recognize and bind to a T-cell. In one aspect the T-cell is a universal CAR-T cell. In another aspect, the T-cell targeting domain is one or more antibodies that recognize cell surface moieties on a T-cell or a universal CAR-T cell. In one aspect, the T-cell targeting domain is one or more antibodies that recognize and bind to CD3 on the surface of a T-cell or universal CAR-T cell.

Described herein is a dual-antibody nanoparticle system in order to improve upon these allogeneic cells and allow for a quicker way to produce CAR-T cells that specifically target a subject's cancer and overcome the manufacturing bottleneck. Nanoparticles can be conjugated with specific antibodies which, in theory, can attach to tumor cells as well as uCAR-T cells. This would eliminate the need to produce specialized allogeneic CAR-T cells and allow for a relatively quick and simple way to modify generic uCAR-T cells to target the patient's tumor (about 48 hours). Results shown here demonstrate the effectiveness of the pairing of functionalized nanoparticles with uCAR-T cells in killing different solid cancers and the minimal off-target activation and toxic side effects on healthy normal cells.

One embodiment described herein is a nanoparticle system comprising (a) at least one tumor cell targeting domain that specifically binds to a cell surface moiety present on a desired target cell (e.g., a tumor or cancer cell) and (b) at least one T-cell targeting domain that specifically binds T-cells or CAR-T cells. In one aspect, the nanoparticle system comprises (a) multiple tumor cell targeting domain (e.g., 2, 3, 4, or more) that specifically bind to different cell surface moieties or antigens on a desired target cell and (b) at least one T-cell targeting domain that specifically binds T-cells or CAR-T cells. In one embodiment, the composition comprises nanoparticles that have at least one tumor cell targeting domain, and at least one T-cell targeting domain on the surface of the nanoparticles. In another embodiment, the nanoparticles further comprise one or more active pharmaceutical ingredient.

The nanoparticle system as disclosed herein redirects T-cells or CAR-T cells to the target cells, where the T-cells mediate lysis of the target cells. As used herein the terms "engages T-cells" or "redirects T-cells" are used interchangeably and refer to the ability of the compositions described herein to bring into close proximity T-cells or CAR-T cells and a target cell having a defined cell surface antigen, through binding to the nanoparticle which recognized both T-cells or CAR-T and the target cell via the respective cell surface moieties. The disclosed compositions and methods can recruit endogenous T-cell or can be pre-loaded with CAR-T cells. The binding of the nanoparticle to both the target cell antigen and to a T-cell or CAR-T cell results in activation of the T-cell or CAR-T cell (e.g., increased cytokine production such as IL-2, IL-6, IL-10, IFN-$\gamma$, or TNF-$\alpha$; increased surface marker expression such as CD69; or increased target cell lysis) and in improved killing or induction of apoptosis of the target cell. A composition of the present disclosure may also comprise a suitable pharmaceutically acceptable carrier known in the art. Components of nanoparticle system are described below.

Nanoparticle

As used herein, the term nanoparticle refers to a particle that has a diameter of less than 1 μm (1000 nm). Nanoparticles used in the systems described herein can be made of metals such as iron, nickel, aluminum, copper, zinc, cadmium, titanium, zirconium, tin, lead, chromium, manganese and cobalt; metal oxides and hydrated oxides such as silicon dioxide, aluminum oxide, chromium oxide, iron oxide, zinc oxide, and cobalt oxide; metal silicates such as of magnesium, aluminum, zinc, lead, chromium, copper, iron, cobalt, and nickel; alloys such as bronze, brass, stainless steel, and so forth. Nanoparticles can also be made of non-metal or organic materials such as cellulose, ceramics, glass, nylon, polystyrene, rubber, plastic, or latex. The base material can be doped with an agent to alter its physical or chemical properties.

In one embodiment, the nanoparticle comprises a silicon dioxide core and comprises a plurality of gold nanospheres coupled to the surface of the silicon dioxide core.

The configuration of nanoparticles can vary from being irregular in shape to being spherical and/or from having an uneven or irregular surface to having a smooth surface. Desired characteristics of nanoparticles can be selected depending on the particular conditions under which they will be prepared and/or used. Nanoparticles may be of uniform or variable size. Particle size distribution can be conveniently determined, for example, using dynamic light scattering.

In some embodiments, nanoparticles have a mean particle diameter of 2-500 nm. Nanoparticles may be substantially spherical in shape and the diameter of a group of nanoparticles may be represented by the average diameter of the nanoparticles in the group. In some embodiments, nanoparticles have a mean particle diameter of 20-400 nm, 30-300 nm, 40-200 nm, 50-100 nm, 30-100 nm, 30-150 nm, 30-200 nm, 50-150 nm, 50-200 nm, 50-300 nm, 40-150 nm, 40-140 nm, 45-130 nm, 40-120 nm, 40-100 nm, 45-140 nm, 45-130 nm or 45-150 nm. In one aspect, the mean particle diameter of a nanoparticle of the present disclosure may be about 45 nm or about 130 nm.

Targeting domains can be conjugated to nanoparticles by various means well-known in the art, including covalent linkage, adsorption, or combinations thereof. In one embodiment, targeting domains are chemically linked to the nanoparticles. In some embodiments, antibodies are bound to nanoparticles coated with anti-immunoglobulin antibodies. In other embodiments, nanoparticles can be conjugated with a coupling agent (e.g., streptavidin) and coupling agent-conjugated-nanoparticles are then mixed with tagged proteins of interest (e.g., biotinylated monoclonal targeting antibodies).

Tumor Cell Targeting Domains

In some embodiments, the nanoparticles disclosed herein comprises at least one tumor cell targeting domains. In other aspects, the nanoparticles comprise 1, 2, 3, 4, 5, or more tumor cell targeting domains. In some embodiments, the nanoparticles comprise multiple a tumor cell targeting domains each specific for a distinct target. As used herein, the term "tumor cell targeting domains" refers to a molecule that may bind to a specific molecule on a target cell, and that directs a nanoparticle to a particular location or cell. As described above, a tumor cell targeting domains may be attached to the surface of a nanoparticle through covalent, non-covalent, or other associations. Non-limiting examples of a tumor cell targeting domain may include synthetic compounds, natural compounds or products, macromolecular entities, and bioengineered molecules, and may include antibodies, antibody fragments, polypeptides, lipids, polynucleotides, and small molecules such as ligands, and hormones.

In an aspect, the tumor cell targeting domain may be an antibody. As used herein, the term "antibody" generally means a polypeptide or protein that recognizes and can bind to an epitope of an antigen. An antibody, as used herein, may be a complete antibody as understood in the art, i.e., consisting of two heavy chains and two light chains, or may be any antibody-like molecule that has an antigen binding region, and includes, but is not limited to, antibody fragments such as Fab', Fab, F(ab')2, single domain antibodies, Fv, and single chain Fv. The term antibody also refers to a polyclonal antibody, a monoclonal antibody, a chimeric antibody, or a humanized antibody. The techniques for preparing and using various antibody-based constructs and fragments are well known in the art. Means for preparing and characterizing antibodies are also well known in the art. See Antibodies: A Laboratory Manual, Cold Spring.

Antibodies that specifically bind to antigens or epitopes present on the desired target cells (e.g., tumor or cancer cells) are used to bring T-cells or CAR-T cells in sufficient proximity to the target cells via the nanoparticle to effect killing of those cells.

Specific binding occurs to the corresponding antigen even in the presence of a heterogeneous population of proteins and other biologics. "Specific binding" of an antibody means that the binds to its target antigen with an affinity that is substantially greater than the antibody's binding to an irrelevant antigen. The relative difference in affinity is often at least 25% greater, more often at least 50% greater, most often at least 100%. The relative difference can be at least

13

2x, at least 5x, at least 10x, at least 25x, at least 50x, at least 100x, at least 1000x, for example.

A nanoparticle can be directed to a variety of target cell types, including tumor cells, depending on the specificity of the tumor cell targeting domain on the nanoparticle. In some embodiments, the tumor cell targeting domain specifically binds to a tumor-associated antigen. Tumor-associated antigens include unique tumor antigens expressed exclusively by the tumor from which they are derived, shared tumor antigens expressed in many tumors but not in normal adult tissues (oncofetal antigens), and tissue-specific antigens expressed also by the normal tissue from which the tumor arose. Tumor-associated antigens can be, for example but not limited to, embryonic antigens, antigens with abnormal post-translational modifications, differentiation antigens, products of mutated oncogenes or tumor suppressors, fusion proteins, or oncoviral proteins.

A variety of tumor-associated antigens are known in the art, and many of these are commercially available. Oncofetal and embryonic antigens include carcinoembryonic antigen and alpha-fetoprotein (usually only highly expressed in developing embryos but frequently highly expressed by tumors of the liver and colon, respectively), MAGE-1 and MAGE-3 (expressed in melanoma, breast cancer, and glioma), placental alkaline phosphatase sialyl-Lewis X (expressed in adenocarcinoma), CA-125 and CA-19 (expressed in gastrointestinal, hepatic, and gynecological tumors), TAG-72 (expressed in colorectal tumors), epithelial glycoprotein 2 (expressed in many carcinomas), pancreatic oncofetal antigen, 5T4 (expressed in gastric carcinoma), alphafetoprotein receptor (expressed in multiple tumor types, particularly mammary tumors), and M2A (expressed in germ cell neoplasia).

Tumor-associated differentiation antigens include tyrosinase (expressed in melanoma) and particular surface immunoglobulins (expressed in lymphomas).

Mutated oncogene or tumor-suppressor gene products include Ras and p53, both of which are expressed in many tumor types, HER2 (expressed in breast and gynecological cancers), EGF-R, estrogen receptor, progesterone receptor, retinoblastoma gene product, myc (associated with lung cancer), ras, p53, nonmutant associated with breast tumors, MAGE-1, and MAGE-3 (associated with melanoma, lung, and other cancers). Fusion proteins include, but are not limited to, BCR-ABL, which is expressed in chromic myeloid leukemia. Non limiting examples of oncoviral proteins include HPV type 16, E6, and E7, which are found in cervical carcinoma.

Non limiting examples of tissue-specific antigens include melanotransferrin and MUC 1 (expressed in pancreatic and breast cancers); CD10 (previously known as common acute lymphoblastic leukemia antigen, or CALLA) or surface immunoglobulin (expressed in B cell leukemias and lymphomas); the a chain of the IL-2 receptor, T cell receptor, CD45R, CD4+/CD8+ (expressed in T cell leukemias and lymphomas); prostate-specific antigen and prostatic acid-phosphatase (expressed in prostate carcinoma); GP 100, MelanA/Mart-1, tyrosinase, gp75/brown, BAGE, and S-100 (expressed in melanoma); cytokeratins (expressed in various carcinomas); and CD19, CD20, and CD37 (expressed in lymphoma).

In one aspect, the one or more tumor cell targeting domains are selected from the group of: an antibody, a multi-specific antibody, a monoclonal antibody, an scFv antibody fragment, a single domain antibody, a heavy chain variable domain (VH), a light chain variable domain (VL), a bispecific antibody, or a bispecific antibody fragment, a multi-specific antibody fragment, Fab, F(ab)'2, Fab', and Fv. antibody fragment, or an equivalent of each thereof. Non-limiting examples of antibodies and fragments and derivatives thereof are of the group of antibodies: anti-HER2; anti-HER3; anti-EGFR; anti-CD3; anti-CD16; anti-CD4; anti-CD8; anti-CD11a; anti-CD19; anti-CD20; anti-CD25; anti-CD33; anti-CD40; anti-CD40L; anti-CD70; anti-CD123; anti-EpCAM; anti-CLL-1; anti-CTLA-4; anti-PD-1; anti-PD-L1; anti-OX40; anti-GITR; anti-ICOS; anti-B7-H3; anti-B7-H4; anti-LAG3; anti-TIM3; anti-PSMA; anti-factor IXa; anti-factor X; and anti-folate receptor, fragments or derivatives thereof.

In another aspect, the tumor cell targeting domain specifically recognizes and binds an immune cell. In a further aspect, the engineered vesicle comprises, or alternatively consists essentially of, or yet further consists of different antigen binding domains, e.g., one or more specific to a cancer or tumor cell and one or more specific to an immune cell.

Examples of tumor cell targeting domains include those that bind an antigen of the group of: a tumor antigen, a cancer antigen, an antigen expressed on an immune cell, activated coagulation factor IX, factor X, an antigen involved in immune regulation such as a cell surface receptor that mediates the reaction of an immune cell (e.g., a T cell, a macrophage or a natural killer cell) or a checkpoint inhibitor, e.g., PDL1, CTLA-4, B7-H3, B7-H4, LAG3, PD1, TIM-3, or a checkpoint activator, e.g., CD40, OX40, GITR, and ICOS.

When the tumor cell targeting domain is specific for a cancer antigen, examples of such include a cancer antigen is selected from the groups of breast cancer, lung cancer, colorectal cancer, kidney cancer, prostate cancer, brain cancer, pancreatic cancer, ovarian cancer, liver cancer, bladder cancer, lymphoma, melanoma, a solid malignant cancer or a blood cancer. Specific examples include HER2 or EGFR expressed on breast cancer or colorectal cancer.

When the tumor cell targeting domain is specific for an immune cell, non-limiting examples of immune cells are selected from the group of: a CD3+ T cell, a CD16+ cell, a CD16+NK cell, a CD4 cell, a CD8 cell, a CD19 cell, a CD20 cell, or a B cell.

In one embodiment, the tumor cell targeting domain comprises one or more antibodies that can recognize and bind to HER2 on tumor or cancer cells. In one embodiment, the tumor cell targeting domain is selected from one or more of those presented in Table 1.

TABLE 1

| Exemplary Tumor Cell Targeting Domains | | | | |
|---|---|---|---|---|
| Name | Brand name | Mfr. | Cat. No. | Alternate Names |
| Biosimilar to Herceptin | Ogivri (trastuzumab-dkst); Herzuma (trastuzumab-pkrb); Ontruzant (trastuzumab-dttb); Trazimera (trastuzumab-qyyp); Kanjinti (trastuzumab-anns) | | | |
| Biosimilar to Herceptin | Human ErbB2/Her2 Antibody | R&D biosystems | MAB1129 | any Human ErbB2/Her2 Antibody |

T-Cell Targeting Domain

In some embodiments, the nanoparticles disclosed herein comprise at least one T-cell targeting domain. As used herein, the term "T-cell targeting domain" refers to a molecule that specifically binds to and/or activates a specific molecule on expressed on T-cells, such as CD3, in order to redirect and/or active them to a desired target, using a nanoparticle as described above. The "antigen-specificity" of a T-cell refers to the fact that the T-cells are subpopulations, e.g., subpopulations of highly effective cytotoxic T-cells specific for, e.g., a viral antigen or an antigen from another pathogen, or subpopulations of helper T-cells. Several types of moieties can be used for this purpose.

In some embodiments, the T-cell targeting domain is an anti-TCR-specific antibody, such as an antibody that specifically binds to a TCR present on a population of T-cells. In one aspect, the T-cell targeting domain is an anti-CD3 antibody. In one embodiment, the tumor cell targeting domain is selected from one or more of those presented in Table 2.

TABLE 2

Exemplary T-cell Targeting Domains

| Name | Brand name | Mfr. | Cat. No. | Alternate Names |
|---|---|---|---|---|
| Biosimilar to anti-CD3 | Teplizumab | Creative biolab | TAB-159 | Teplizumab; 876387-05-2; MGA031; hOKT3gamma 1(Ala-Ala); CD3D; CD3d molecule, delta (CD3-TCR complex); CD3d antigen, delta polypeptide (TiT3 complex), T3D; T-cell surface glycoprotein CD3 delta chain; CD3 delta; OKT3, delta chain; CD3 antigen, delta subunit; T-cell R |
| Biosimilar to anti-CD3 | InVivoMAb anti-human CD3 | BioXcell | BE0001-2 | |
| Biosimilar to antiCD3 CD3 antigen, delta subunit CD3 CD3d antigen CD3d antigen, delta polypeptide (TiT3 complex) CD3d molecule, delta (CD3-TCR complex) CD3-DELTA CD3e antigen CD3e antigen, epsilon polypeptide (TiT3 complex) CD3e molecule, epsilon (CD3-TCR complex) CD3e CD3-epsilon CD3g antigen CD3g antigen, gamma polypeptide (TiT3 complex) CD3g molecule, epsilon (CD3-TCR complex) CD3g molecule, gamma (CD3-TCR complex) CD3G CD3-GAMMA FLJ17620 FLJ17664 FLJ18683 FLJ79544 FLJ94613 IMD18 MGC138597 T3DOKT3, delta chain T3E T-cell antigen receptor complex, epsilon subunit of T3 T-cell receptor T3 | CD3 Antibody (Hu113) | novus biologicals | MAB9929-SP | CD-antigen: CD3e |

TABLE 2-continued

| Exemplary T-cell Targeting Domains | | | | |
|---|---|---|---|---|
| Name | Brand name | Mfr. | Cat. No. | Alternate Names |
| delta chain<br>T-cell surface<br>antigen T3/Leu-4<br>epsilon chain<br>T-cell surface<br>glycoprotein CD3<br>delta chain<br>T-cell surface<br>glycoprotein CD3<br>epsilon chain<br>TCRE | | | | |

In some embodiments, the T-cell targeting domain is an MHC class I-immunoglobulin complex, an MHC class I molecule (e.g., a soluble monomer or multimer), an MHC class II molecule (e.g., a soluble monomer or multimer), or an MHC class II-immunoglobulin complex. Such moieties comprise an antigenic peptide to which the T-cell is directed.

In some embodiments, the T-cell targeting domain is an MHC class I-immunoglobulin complex comprising (i) an immunoglobulin molecule comprising two immunoglobulin heavy chains and two immunoglobulin light chains; and (ii) two MHC class I molecules, each comprising an a chain and a β2 microglobulin. Each a chain comprises α1, α2, and α3 domains, and the α1 and α2 domains of each a chain form a peptide binding cleft. The N terminus of each immunoglobulin heavy chain is linked to the N terminus of each α3 domain, and the peptide binding cleft comprises an antigenic peptide recognized by the T-cell.

In some embodiments, the T-cell targeting domain is an MHC class I molecule comprising an antigenic peptide recognized by the T-cell. In some embodiments, the MHC class I molecule is a soluble monomeric form. In some embodiments, the MHC class I molecule is a soluble multimeric form.

In some embodiments, the T-cell targeting domain is an MHC class II molecule comprising an antigenic peptide recognized by the T-cell. In some embodiments, the MHC class II molecule is a soluble monomeric form. In some embodiments, the MHC class II molecule is a soluble multimeric form.

CAR-T Cells

CAR-T cells useful for the applications described herein can be laboratory made or commercially available. A number of commercially available CAR-T cells are available from ProMab Biotechnologies (Richmond, CA). Any of these CAR-T cells can be used as long the CAR-T cells do not have a CAR targeting HER2 or an antigen that the NPs targets on the tumor. Similarly, the appropriate activator specific to the CAR-T cell chosen can be used to induce cytotoxicity at the anchored site. For example, for the CAR-T cell: CD37-TM28-CD28-CD3 ZETA (PM-CAR1052-1M) a CD37 would be used as the activator of the CAR-T cells. Table 3 provides a listing of exemplary commercially available CAR-T cells.

TABLE 3

| Exemplary Commercially Available CAR-T Cells<br>(ProMab, Richmond CA) | |
|---|---|
| CAR-T Cel Description | Catalog No. |
| Mock scFv-CD28-CD3ζ | PM-CAR1000-1M |
| CD19 scFv-CD28-CD3ζ | PM-CAR1001-1M |

TABLE 3-continued

| Exemplary Commercially Available CAR-T Cells<br>(ProMab, Richmond CA) | |
|---|---|
| CAR-T Cel Description | Catalog No. |
| CD19 scFv-4-1BB-CD3ζ | PM-CAR1002-1M |
| CD19 scFv-CD28-4-1BB-CD3ζ | PM-CAR1003-1M |
| CD19 scFv-CD28-4-1BB | PM-CAR1004-1M |
| CD19scFv-TM-41BB-CD3z-T2A-GFP | PM-CAR1005-1M |
| iCas9-T2A-antiCD19 scFv-CD28-CD3ζ | PM-CAR1006-1M |
| CD19 scFv-FLAG-CD28-CD3ζ | PM-CAR1007-1M |
| no scFv-CD28-CD3ζ | PM-CAR1008-1M |
| CD19 scFv-CD28 | PM-CAR1009-1M |
| iCas9 HA-T2A-antiCD19scFv-CD28-CD3ζ-<br>GGGS-FLAG | PM-CAR1010-1M |
| Mesothelin scFv-CD28-CD3ζ (2nd) | PM-CAR1011-1M |
| Mesothelin scFv-CD28-4-1BB-CD3ζ (3rd) | PM-CAR1012-1M |
| Mesothelin scFv-4-1BB-CD3ζ (2nd) | PM-CAR1013-1M |
| Mesothelin scFv-4-1BB-CD3ζ-FLAG | PM-CAR1014-1M |
| Mesothelin scFv-FLAG-4-1BB-CD3ζ (2nd) | PM-CAR1015-1M |
| VEGFR2 scFv-CD28-CD3ζ | PM-CAR1016-1M |
| GPC3 scFv-CD28-CD3ζ | PM-CAR1017-1M |
| CD133 scFv-CD28-CD3ζ | PM-CAR1018-1M |
| EpCAM1 scFv-CD28-CD3ζ | PM-CAR1019-1M |
| EpCAM scFv-CD28-CD3ζ * Nhel restriction site<br>introduced, N-terminal of scFV (amino acids: AS) | PM-CAR1020-1M |
| EGFR scFv-CD28-CD3ζ | PM-CAR1021-1M |
| EGFR scFv-4-1BB-CD3ζ | PM-CAR1022-1M |
| EGFR scFv-TM28-GITR-CD3ζ | PM-CAR1023-1M |
| Her2 scFv-CD28-CD3ζ | PM-CAR1024-1M |
| EGFR scFv-TM28-CD3ζ-GITR | PM-CAR1025-1M |
| CD33 scFv-TM28-CD28-CD3ζ | PM-CAR1026-1M |
| CD38 scFv-TM28-CD28-CD3ζ | PM-CAR1027-1M |
| CD138 scFv-Beam1-TM28-CD28-CD3ζ | PM-CAR1028-1M |
| CD22 scFv-TM28-CD28-CD3ζ | PM-CAR1029-1M |
| CD22 scFv-TM8-4-1BB-CD3ζ | PM-CAR1030-1M |
| BCMA-4-CD28-CD3ζ | PM-CAR1031-1M |
| CD4 scFv-Beam1-TM28-CD28-CD3ζ | PM-CAR1032-1M |
| Humanized BCMA-2 scFv-TM28-CD28-CD3ζ | PM-CAR1033-1M |
| Mouse ROR-1 scFv-TM28-CD28-CD3ζ | PM-CAR1034-1M |
| CD19 scFv-CD22 scFv-4-1BB-CD3ζ | PM-CAR1035-1M |
| Humanized CEA scFv-TM28-CD28-CD3ζ | PM-CAR1036-1M |
| BCMA-4 scFv-TM8-4-1BB-CD3ζ | PM-CAR1037-1M |
| NGFR scFv-TM28-CD28-CD3ζ | PM-CAR1038-1M |
| MCAM scFv-TM28-CD28-CD3ζ | PM-CAR1039-1M |
| CD47 scFv-TM28-CD28-CD3ζ | PM-CAR1040-1M |
| Humanized CD47 scFv-TM28-CD28-CD3ζ | PM-CAR1041-1M |
| Humanized CD19 scFv-TM28-CD28-CD3ζ | PM-CAR1042-1M |
| Humanized CD19 scFv-Beam1-TM28-CD28-<br>CD3ζ | PM-CAR1043-1M |
| Human ROR1 scFv-TM28-4-1BB-CD3ζ | PM-CAR1044-1M |
| PDL-1 scFv-TM28-CD28-CD3ζ | PM-CAR1045-1M |
| CD123 scFv-TM28-CD28-CD3ζ | PM-CAR1046-1M |
| CD22 scFv-Beam2-TM28-CD28-CD3ζ | PM-CAR1047-1M |
| CD19 scFv-Beam2-TM28-CD28-CD3ζ | PM-CAR1048-1M |
| CD19 scFv-CD22 scFv-4-1BB-CD3-T2A-tEGFR<br>(Suicide switch) | PM-CAR1049-1M |
| CD19 scFv-CD22 scFv-4-1BB-CD3-T2A-RQR8 | PM-CAR1050-1M |

TABLE 3-continued

Exemplary Commercially Available CAR-T Cells
(ProMab, Richmond CA)

| CAR-T Cel Description | Catalog No. |
|---|---|
| (Ritiximab suicide switch) | |
| BCMA-2 scFv-TM-CD28-CD3ζ | PM-CAR1051-1M |
| CD37 scFv-TM28-CD28-CD3ζ | PM-CAR1052-1M |
| CD37 scFv-TM28-4-1BB-CD3ζ | PM-CAR1053-1M |
| CD19 scFv-TM28-GITR-CD3ζ | PM-CAR1054-1M |
| CD19 scFv-TM8-GITR-CD3ζ | PM-CAR1055-1M |
| CD33 scFv-Beam 2-TM28-CD28-CD3ζ | PM-CAR1056-1M |
| CS1 scFv-TM28-CD28-CD3ζ | PM-CAR1057-1M |
| B7H4 scFv-TM28-CD28-CD3ζ | PM-CAR1058-1M |
| CD24 scFv-TM28-CD28-CD3ζ | PM-CAR1059-1M |
| Mesothelin scFv-TM28-CD28-4-1BB-CD3ζ | PM-CAR1060-1M |
| 3x Beam2-TM28-CD28-CD3ζ (Mock) | PM-CAR1061-1M |
| CD20 scFv-TM28-CD28-CD3ζ | PM-CAR1062-1M |
| Her2 scFv-4-1BB-CD3Z-EGFRt | PM-CAR1063-1M |
| Her2 scFv-4-1BB-CD3Z-GFP | PM-CAR1064-1M |

In one embodiment, a nanoparticle delivery system described herein may be used to deliver an active agent to a cell or site of interest. In an aspect, a nanoparticle described herein may encapsulate an active agent. As used herein "active agents" may be therapeutic agents, diagnostic agents, or a combination thereof. Non-limiting examples of an active agent may include proteasome inhibitors, histone deacetylase inhibitors, chemotherapeutic agents, immuno-modulating agents, or other agents that may be toxic to or kill cancer cells. Non-limiting examples of proteasome inhibitors may include bortezomib, carfilzomib, marizomib, ixazomib, or MLN9708. Non-limiting examples of a histone deacetylase inhibitor may be panobinostat, vorinostat, zolinza, romidepsin, or Istodax. Non limiting examples of chemotherapeutic agents may be doxorubicin, melphalan, vincristine, cyclophosphamide, etoposide, or bendamustine. Non-limiting examples of immunomodulating agents may be thalidomide, lenalidomide, or pomalidomide.

A nanoparticle described herein may carry an active agent. The active agent, which may be a therapeutic agent may be associated with the surface of, encapsulated within, surrounded by, or dispersed throughout the nanoparticle. In a preferred aspect described herein, an active agent is encapsulated within the core of a nanoparticle.

A pharmaceutical composition of the nanoparticle system described herein may also comprise one or more nontoxic pharmaceutically acceptable carriers, adjuvants, excipients, and vehicles as desired. As used herein, the language "phar-maceutically acceptable carrier" is intended to include any and all solvents, dispersion media, coatings, antibacterial and antifungal agents, isotonic and absorption delaying agents, and the like, compatible with pharmaceutical admin-istration. The use of such media and agents for pharmaceu-tically active substances is well known in the art. Except insofar as any conventional media or agent is incompatible with a nanoparticle system described herein, use thereof in the compositions is contemplated. Supplementary active compounds may also be incorporated into the compositions.

A pharmaceutical composition of the nanoparticle system described herein may be formulated to be compatible with its intended route of administration. Suitable routes of administration may include parenteral, oral, pulmonary, transdermal, transmucosal, and rectal administration. The term parenteral, as used herein, includes subcutaneous, intravenous, intramuscular, intrathecal, or intrasternal injec-tion, or infusion techniques.

Solutions or suspensions used for parenteral, intradermal, or subcutaneous application may include the following components: a sterile diluent such as water for injection, saline solution, fixed oils, polyethylene glycols, glycerine, propylene glycol or other synthetic solvents; antibacterial agents such as benzyl alcohol or methyl parabens; antioxi-dants such as ascorbic acid or sodium bisulfite; chelating agents such as ethylenediaminetetraacetic acid; buffers such as acetates, citrates or phosphates, and agents for the adjust-ment of tonicity such as sodium chloride or dextrose. The pH may be adjusted with acids or bases, such as hydrochloric acid or sodium hydroxide. The parenteral preparation may be enclosed in ampoules, disposable syringes or multiple dose vials made of glass or plastic.

Pharmaceutical Compositions

In one embodiment, the nanoparticle system described herein is formulated to be compatible with parenteral admin-istration. For instance, pharmaceutical compositions suitable for injectable use may include sterile aqueous solutions (where water soluble) or dispersions and sterile powders for the extemporaneous preparation of sterile injectable solu-tions or dispersion. For intravenous administration, suitable carriers include physiological saline, bacteriostatic water, Cremophor EL (BASF; Parsippany, N.J.), or phosphate buffered saline (PBS). In an exemplary embodiment, a pharmaceutical composition of the nanoparticle system described herein is formulated with phosphate buffered saline (PBS).

In all cases, a composition may be sterile and may be fluid to the extent that easy syringe ability exists. A composition may be stable under the conditions of manufacture and storage and may be preserved against the contaminating action of microorganisms such as bacteria and fungi. The carrier may be a solvent or dispersion medium containing, for example, water, ethanol, polyol (for example, glycerol, propylene glycol, and liquid polyethylene glycol, and the like), and suitable mixtures thereof. The proper fluidity may be maintained, for example, by the use of a coating such as lecithin, by the maintenance of the required particle size in the case of dispersion, and by the use of surfactants. Pre-vention of the action of microorganisms may be achieved by various antibacterial and antifungal agents, for example, parabens, chlorobutanol, phenol, ascorbic acid, thimerosal, and the like. In many cases, it may be preferable to include isotonic agents, for example, sugars, polyalcohols such as mannitol, sorbitol, or sodium chloride, in the composition. Prolonged absorption of the injectable compositions may be brought about by including in the composition an agent which delays absorption, for example, aluminum monoste-arate and gelatin.

Sterile injectable solutions may be prepared by incorpo-rating the active compound in the required amount in an appropriate solvent with one or a combination of ingredients enumerated above, as required, followed by filtered steril-ization. Generally, dispersions are prepared by incorporating the active compound into a sterile vehicle which contains a basic dispersion medium and the required other ingredients from those enumerated above. In the case of sterile powders for the preparation of sterile injectable solutions, the pre-ferred methods of preparation are vacuum drying and freeze-drying, which yields a powder of the active ingredient plus any additional desired ingredient from a previously sterile-filtered solution thereof.

Systemic administration may also be by transmucosal or transdermal means. For transmucosal or transdermal admin-istration, penetrants appropriate to the barrier to be perme-ated are used in the formulation. Such penetrants are generally known in the art, and may include, for example, for transmucosal administration, detergents, bile salts, and fusidic acid derivatives. Transmucosal administration may be accomplished through the use of nasal sprays or suppositories. For transdermal administration, the active compounds are formulated into ointments, salves, gels, or creams as generally known in the art. The compounds may also be prepared in the form of suppositories (e.g., with conventional suppository bases such as cocoa butter and other glycerides) or retention enemas for rectal delivery.

In one embodiment, the nanoparticle system described herein may be prepared with carriers that will protect the compound against rapid elimination from the body, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, and polylactic acid.

Methods

One embodiment described herein is the use of the compositions and methods for cancer immunotherapy and the nanoparticle system displays an antigen binding domain for the cancer cell and a T-cell targeting domain specific for an immune cell. In one aspect, the immune cell is a T-cell or CAR-T cell. In another aspect, the nanoparticle system comprises, or alternatively consists essentially of, or further consists of a therapeutic agent to treat the cancer.

Another embodiment described herein is a method of treating cancer in a subject in need by administration of a therapeutically effective amount of a composition comprising the nanoparticle system as described herein, so as to recognize an antigen on cancer cells and the engage CAR-T cells. Upon activation, the CAR-T cells induce tumor cell death, thereby reducing cancer progression. The therapeutically effective amount can also redirect T cells to tumor cells which results in an efficacious immune response (e.g., activation of T cells) against a tumor and/or produce improved tumor cell killing for heterogeneous tumors.

In one embodiment, the nanoparticle system described herein has an in vivo half-life of at least 10 hours, at least 15 hours, at least 20 hours, at least 25 hours, at least 30 hours, at least 35 hours, at least 40 hours, at least 50 hours, at least 55 hours, at least 60 hours, at least 65 hours, at least 70 hours, at least 75 hours, at least 80 hours, at least 85 hours, at least 90 hours, at least 95 hours. In one aspect, the nanoparticle system described herein has an in vivo half-life of about 60 hours.

Another embodiment described herein encompasses administering a therapeutically effective amount of the nanoparticle system to a subject in need thereof.

Another embodiment described herein is a nanoparticle system formulated to be compatible with its intended route of administration. Suitable routes of administration include parenteral, oral, pulmonary, transdermal, transmucosal, and rectal administration. In one embodiment, the pharmaceutical composition described herein is administered by injection.

The amount and concentration of the composition administered to a subject will depend in part on the subject and the reason for the administration. Methods for determining optimal amounts are known in the art. Generally, a safe and effective amount of a nanoparticle composition is, for example, that amount that would cause the desired therapeutic effect in a subject while minimizing undesired side effects. In various embodiments, an effective amount of a nanoparticle composition described herein can substantially inhibit cancer progression, slow the progress of cancer, or limit the development of cancer.

Compositions described herein are typically administered to a subject in need thereof in an amount sufficient to provide a benefit to the subject. This amount is defined as a "therapeutically effective amount." A therapeutically effective amount may be determined by the efficacy or potency of the particular composition, the disorder being treated, the duration or frequency of administration, the method of administration, and the size and condition of the subject, including that subject's particular treatment response. A therapeutically effective amount may be determined using methods known in the art, and may be determined experimentally, derived from therapeutically effective amounts determined in model animals such as the mouse, or a combination thereof. Additionally, the route of administration may be considered when determining the therapeutically effective amount. In determining therapeutically effective amounts, one skilled in the art may also consider the existence, nature, and extent of any adverse effects that accompany the administration of a particular compound in a particular subject.

When used in the treatments described herein, a therapeutically effective amount of a nanoparticle composition can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to recognize an antigen on cancer cells and the engage T cells, reducing cancer progression.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts For example, it is typical to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of a nanoparticle composition can occur as a single event or over a time course of treatment. For example, a nanoparticle composition can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities cancer.

A nanoparticle composition can be administered simultaneously or sequentially with another agent, such as an antibiotic, an anti-inflammatory, or another agent. For example, a nanoparticle composition can be administered simultaneously with another agent, such as an antibiotic or an anti-inflammatory.

In one embodiment, the nanoparticle system described herein is used to treat a neoplasm or cancer. The neoplasm may be malignant or benign, the cancer may be primary or metastatic; the neoplasm or cancer may be early stage or late stage. A cancer or a neoplasm may be treated by delivering nanoparticles carrying a therapeutic agent to at least one cancer cell in a subject. The cancer or neoplasm may be treated by slowing cancer cell growth or killing cancer cells.

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intramuscular, intraperitoneal, intravenous, subcutaneous, intranasal, epidural, ophthalmic, buccal, or rectal administration.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 jam), nanospheres (e.g., less than 1 μm), microspheres (e.g., 1-100 μm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposome. Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

In one embodiment, the nanoparticle delivery system described herein may treat a cancer or a neoplasm by delivering a therapeutic nanoparticle to a cancer cell in a subject in vivo. Non-limiting examples of neoplasms or cancers that may be treated with a method described herein may include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas), breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sezary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-cell lymphoma (cutaneous), T-cell leukemia and lymphoma, testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), unknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, or Wilms tumor (childhood).

In other aspects, a nanoparticle delivery system described herein may deliver a therapeutic nanoparticle to a cancer cell in vitro. A cancer cell may be a cancer cell line cultured in vitro. In some alternatives of the embodiments, a cancer cell line may be a primary cell line that is not yet described.

Methods of preparing a primary cancer cell line utilize standard techniques known to individuals skilled in the art. In other alternatives, a cancer cell line may be an established cancer cell line. A cancer cell line may be adherent or non-adherent, or a cell line may be grown under conditions that encourage adherent, non-adherent or organotypic growth using standard techniques known to individuals skilled in the art. A cancer cell line may be contact inhibited or non-contact inhibited.

In some embodiments, the cancer cell line may be an established human cell line derived from a tumor. Non-limiting examples of cancer cell lines derived from a tumor may include the MM cell lines MM.1S, H929, and RPMI, osteosarcoma cell lines 143B, CAL-72, G-292, HOS, KHOS, MG-63, Saos-2, or U-2 OS; the prostate cancer cell lines DU145, PC3 or Lncap; the breast cancer cell lines MCF-7, MDA-MB-438 or T47D; the myeloid leukemia cell line THP-1, the glioblastoma cell line U87; the neuroblastoma cell line SHSYSY; the bone cancer cell line Saos-2; the colon cancer cell lines WiDr, COLO 320DM, HT29, DLD-1, COLO 205, COLO 201, HCT-15, SW620, LoVo, SW403, SW403, SW1116, SW1463, SW837, SW948, SW1417, GPC-16, HCT-8, HCT 116, NCI-H716, NCI-H747, NCI-H508, NCI-H498, COLO 320HSR, SNU-C2A, LS 180, LS 174T, MOLT-4, LS513, LS1034, LS411N, Hs 675.T, CO 88BV59-1, Co88BV59H21-2, Co88BV59H21-2V67-66, 1116-NS-19-9, TA 99, AS 33, TS 106, Caco-2, HT-29, SK-CO-1, SNU-C2B or SW480; B16-F10, RAW264.7, the F8 cell line, or the pancreatic carcinoma cell line Panc1. In an exemplary embodiment, a method described herein may be used to contact a cell of a MM cell line.

Kits

Another embodiment described herein are kits of the compositions described herein for therapeutic or research use. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components can comprise a nanoparticle composition described herein, or components of a nanoparticle system as described herein. As another example, the components can be conjugated with biotin or avidin. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal, or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate or may be supplied as an electronic medium. Detailed instructions may be physically associated with the kit or a user may be directed to an Internet web site specified by the manufacturer or distributor of the kit.

It will be apparent to one of ordinary skill in the relevant art that suitable modifications and adaptations to the compositions, formulations, methods, processes, and applications described herein can be made without departing from the scope of any embodiments or aspects thereof. The compositions and methods provided are exemplary and are not intended to limit the scope of any of the specified embodiments. All of the various embodiments, aspects, and options disclosed herein can be combined in any variations or iterations. The scope of the compositions, formulations, methods, and processes described herein include all actual or potential combinations of embodiments, aspects, options, examples, and preferences herein described. The exemplary compositions and formulations described herein may omit any component, substitute any component disclosed herein, or include any component disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. Furthermore, the foregoing discussion discloses and describes merely exemplary embodiments. All patents and publications cited herein are incorporated by reference herein for the specific teachings thereof.

Various embodiments and aspects of the inventions described herein are summarized by the following clauses:

Clause 1. A therapeutic composition comprising:
a nanoparticle system comprising a silicon dioxide core comprising on the surface a plurality of gold nanospheres conjugated to one or more tumor cell targeting domains and one or more T-cell targeting domains.

Clause 2. The composition of clause 1, wherein the one or more tumor cell targeting domains comprise one or more tumor cell targeting antibodies.

Clause 3. The composition of clause 2, wherein the tumor cell targeting antibodies bind HER2.

Clause 4. The composition of any one of clauses 1-3, wherein the one or more T-cell targeting domains comprise one or more T-cell targeting antibodies.

Clause 5. The composition of clause 4, wherein the T-cell targeting antibodies bind CD3.

Clause 6. The composition of any one of clauses 1-5, wherein the one or more tumor cell targeting domains are conjugated to the silicon dioxide core.

Clause 7. The composition of any one of clauses 1-6, wherein the one or more T-cell targeting domains are conjugated to the plurality of gold nanospheres.

Clause 8. The composition of any one of clauses 1-7, wherein the tumor cell is from breast, ovarian, or prostate tissue.

Clause 9. The composition of any one of clauses 1-8, wherein the T-cell is a CAR-T cell.

Clause 10. The composition of any one of clauses 1-9, wherein the silicon dioxide core comprises a mean particle diameter ranging from about 20 nm to about 200 nm.

Clause 11. The composition of any one of clauses 1-10, wherein the silicon dioxide core comprises a mean particle diameter ranging from about 40 nm to about 150 nm.

Clause 12. The composition of any one of clauses 1-11, wherein the plurality of gold nanospheres comprises about 50 gold nanospheres to about 100 gold nanospheres.

Clause 13. A method for targeting a T-cell to the vicinity of a tumor cell, the method comprising:
contacting a surface of a T-cell and a surface of a tumor cell with a nanoparticle system comprising a silicon dioxide core comprising on the surface a plurality of gold nanospheres conjugated to one or more tumor cell targeting domains and one or more T-cell targeting domains.

Clause 14. The method of clause 13, wherein the one or more tumor cell targeting domains comprise one or more tumor cell targeting antibodies.

Clause 15. The method of clause 14, wherein the tumor cell targeting antibodies bind HER2 on the surface of the tumor cell.

Clause 16. The method of any one of clauses 13-15, wherein the one or more T-cell targeting domains comprise one or more T-cell targeting antibodies.

Clause 17. The method of clause 16, wherein the T-cell targeting antibodies bind CD3 on the surface of the T-cell.

Clause 18. The method of any one of clauses 13-17, wherein the tumor cell is from breast, ovarian, or prostate tissue.

Clause 19. The method of any one of clauses 13-18, wherein the T-cell is a CAR-T cell.

Clause 20. The method of any one of clauses 13-19, wherein the method induces tumor cell death.

Clause 21. A method for inducing tumor cell death in a subject, the method comprising:
administering a therapeutically effective amount of a nanoparticle system comprising a silicon dioxide core comprising on the surface a plurality of gold nanospheres conjugated to one or more tumor cell targeting domains and one or more T-cell targeting domains, wherein the nanoparticle system targets a T-cell to the vicinity of a tumor cell and increases T-cell-mediated death of the tumor cell relative to a subject who has not been administered the nanoparticle system.

Clause 22. The method of clause 21, wherein the one or more tumor cell targeting domains comprise one or more tumor cell targeting antibodies.

Clause 23. The method of clause 22, wherein the tumor cell targeting antibodies bind HER2 on the surface of the tumor cell in the subject.

Clause 24. The method of any one of clauses 21-23, wherein the one or more T-cell targeting domains comprise one or more T-cell targeting antibodies.

Clause 25. The method of any one of clauses 21-24, wherein the T-cell targeting antibodies bind CD3 on the surface of the T-cell in the subject.

Clause 26. The method of any one of clauses 21-25, wherein the subject has breast cancer, ovarian cancer, prostate cancer, or another cancer with high expression of HER2.

Clause 27. The method of any one of clauses 21-26, wherein the T-cell is a CAR-T cell.

Clause 28. A process for manufacturing a nanoparticle system comprising a silicon dioxide core comprising on the surface a plurality of gold nanospheres conjugated to one or more tumor cell targeting domains and one or more T-cell targeting domains, the process comprising:

(a) synthesizing the silicon dioxide core;

(b) synthesizing the plurality of gold nanospheres;

(c) immobilizing the plurality of gold nanospheres to the surface of the silicon dioxide core;

(d) conjugating the one or more tumor cell targeting domains to the surface of the silicon dioxide core; and (e) conjugating the one or more T-cell targeting domains to the plurality of gold nanospheres.

Clause 29. The process of clause 28, wherein the silicon dioxide core is synthesized by performing a sol-gel method.

Clause 30. The process of clause 28 or 29, wherein the plurality of gold nanospheres is synthesized by performing alkaline reduction at room temperature.

Clause 31. The process of any one of clauses 28-30, wherein the one or more tumor cell targeting domains comprise one or more tumor cell targeting antibodies that binds HER2.

Clause 32. The process of any one of clauses 28-31, wherein the one or more T-cell targeting domains comprise one or more T-cell targeting antibodies that bind CD3.

Clause 33. The process of any one of clauses 28-32, wherein the silicon dioxide core comprises a mean particle diameter ranging from about 20 nm to about 200 nm.

Clause 34. The process of any one of clauses 28-33, wherein the silicon dioxide core comprises a mean particle diameter ranging from about 40 nm to about 150 nm.

Clause 35. The process of any one of clauses 28-34, wherein the plurality of gold nanospheres comprises about 50 gold nanospheres to about 100 gold nanospheres.

Clause 36. A nanoparticle system comprising a silicon dioxide core comprising on the surface a plurality of gold nanospheres conjugated to one or more tumor cell targeting domains and one or more T-cell targeting domains manufactured by the process of any one of clauses 28-35.

Clause 37. Use of a nanoparticle system comprising a silicon dioxide core comprising on the surface a plurality of gold nanospheres conjugated to one or more tumor cell targeting domains and one or more T-cell targeting domains for inducing tumor cell death.

REFERENCES

1. American Cancer Society, "Cancer Facts and FIGS. 2020" (2020); (www.cancer.org/research/cancer-facts-statistics/all-cancer-facts-figures/cancer-facts-figures-2020.html).

2. Feins et al., "An introduction to chimeric antigen receptor (CAR) T-cell immunotherapy for human cancer," *Am. J. Hematol.* 94:3-9 (2019).

3. Rafiq et al., "Engineering strategies to overcome the current roadblocks in CAR T cell therapy," *Nat. Rev. Clin. Oncol.* 17:147-167 (2020).

4. Qingyang et al., "CAR-T Cell Therapy in Cancer: Tribulations and Road Ahead," *J. Immunol. Res.* 2020:1924379 (2020).

5. Fesnak et al., "Production of Chimeric Antigen Receptor T cells," Stemcell™ Technologies (2017); (www.stemcell.com/media/files/wallchart/10000009078-Production_ of_Chimeric_Antigen_Receptor_T_Cells.pdf).

6. Depil et al. "'Off-the-shelf' allogeneic CAR T cells: development and challenges," *Nat. Rev. Drug Discov.* 19:185-199 (2020).

7. Stöber et al., "Controlled growth of monodisperse silica spheres in the micron size range," *J. Colloid Interface Sci.* 26 (1): 62-69 (1968).

8. Wang et al., "Volume labeling with Alexa Fluor dyes and surface functionalization of highly sensitive fluorescent silica (SiO₂) nanoparticles," *Nanoscale* 5:10369-10375 (2013).

9. Hopf et al., "Phage-mimicking antibacterial core-shell nanoparticles," *Nanoscale Adv.* 1:4812-2816 (2019).

10. Nghiem et al., "Preparation and characterization of silica-gold core-shell nanoparticles," *J. Nanopart. Res.* 15:2091 (2013).

EXAMPLES

Example 1

Silica Core Synthesis and Silanization

The Stöber method of hydrolysis and condensation of TEOS was utilized to synthesize monodispersed silica cores [7]. To make the silica particles, 30 mL 200 proof ethanol, 6 mL deionized (DI) water, 1.8 mL of 20% w/v $NH_4OH$ in water were stirred with a 1-inch stir bar in a 250 mL glass beaker. Overhead lighting in the laboratory was turned off to optimize conditions for fluorescence. The remainder of the synthesis was performed in the dark. While spinning, 0.9 mL tetraethyl orthosilicate (TEOS) was added with 225 µL RITC-APTES-THF (0.027 M RITC-APTES in THF). The glass beaker was covered and set to stir overnight at room temperature. RITC-$SiO_2$ core solution was centrifuged at 9000 RPM for 30 minutes at room temperature to separate synthesized NPs to form a pellet on the bottom and separate from supernatant. The NP pellet was washed, sonicated (20 s at 40% amplitude), and rinsed with 10 mL ethanol twice by centrifugation. $SiO_2$ cores were resuspended in 25 mL ethanol and transferred into a 250 mL glass beaker. 5 mL DI was added and set to spin. To allow for gold nanospheres to attach to $SiO_2$ cores, 1 mL APTES was added while solution was stirring and was covered and left to stir overnight. The RITC-$SiO_2$-APTES cores were centrifuged at 9000 RPM for 30 minutes at room temperature and separated from the supernatant. The amine-functionalized nanoparticle pellets were washed, sonicated (20 s at 40% amplitude), and rinsed with 10 mL ethanol twice by centrifugation at 9000 RPM. After the last rinse, the centrifuged pellet was resuspended in 10 ml DI water and sonicated (20 s at 40% amplitude). An additional 20 mL DI water was added and mixed into a beaker to bring the volume of RITC-$SiO_2$-APTES core solution to 30 mL.

Alternatively, non-fluorescent silica core particles can be produced using only 1.125 ml TEOS in the absence of RITC-APTES-THF.

Gold Nanosphere Synthesis and Conjugation to RITC Silica Cores

Gold nanospheres were synthesized using a gold nanosphere protocol with adjusted amounts of reagents [8]. 1 43.16 mL DI water, 427 µL NaOH (1 M), 3.21 mL sodium citrate dehydrate (68 mM), and 1.07 mL THPC (Tetrakis (hydroxymethyl)phosphonium chloride) (85 mM) were stirred for 10 minutes at room temperature. Subsequently, 2.14 mL gold chloride (25 mM) was added and stirred overnight. In a 1:1.5 RITC-SiO$_2$-APTES core solution: gold nanosphere solution (v/v), while gold nanosphere solution was still stirring, 45 mL of gold nanosphere solution was pipetted to the beaker containing 30 mL of RITC-SiO$_2$-APTES core solution. RITC-SiO$_2$@Au nanoparticle (NP) solution was stirred overnight in the dark. Then, the RITC-SiO$_2$@Au NP solution was centrifuged at 9000 RPM for 15 minutes at room temperature, followed by two cycles of washing-sonication-centrifugation in 10 mL DI water.

Nanoparticle Synthesis

Nanoparticle synthesis took 4 days to complete using a slightly modified version of the silica core synthesis protocol [9]. Silica cores were synthesized by a sol-gel method as described above (Stöber process). Alkaline reduction was performed at room temperature to synthesize gold nanospheres. In a multistep process derived from established chemistry, the gold nanospheres were immobilized on the silica cores [10]. Rhodamine B-Iso-thiocyanate (RITC)-APTES-THF fluorescence was added to the NPs. NPs were then conjugated with anti-HER2 antibodies attached to the silica NP surface and anti-CD3 antibodies attached to the gold nanospheres.

Attachment of Anti-HER2 Antibody to NP's

A 6 mL aliquot of RITC-SiO$_2$@Au NP (1% w/v silica) was solubilized in 0.5 mL DMSO. 20 mg of NHS-azide was then added and spun overnight at room temperature. The solution was then combined with 15 mL DI water and spun down at 7000 RPM for 30 minutes. 15 mL additional DI water was added, and a second spin was down at 7000 RPM molecular weight cut off membrane for 35 minutes. The solution was then resuspended in 2 mL PBS buffer. 2 mL of the resuspended herceptin and DBCO-NHS was added to 3 mL of the previously made solution of NP's with azides in 3 mL of buffer. This solution was spun at 4° C. to allow covalent bonding between the azide and the anti-HER2. It was spun in 15 mL PBS at 7000 RPM and 8° C. After spinning, the supernatant was stored in an opaque 15 ml tube for a bicinchoninic (BCA) protein assay. NHS-DBCO and NHS-azide was aliquoted in DMSO and frozen in a drybox.

Attachment of Anti-CD3 Antibody to NP's

The previous conjugated product of NP's and anti-HER2 was first spun and linked for 30 minutes at room temperature, then stored at 4° C. for 3.5 hours. 2.5 mL PBS buffer was added to 0.2 mg anti-CD3 antibody, which was then activated with 0.1-0.2 mg thiol polyethylene glycol (PEG) NHS in 2.5 mL PBS buffer. This solution was then spun at 4° C. overnight. Then, the solution was spun down in 10 mL total buffer at 4000 RPM in a fixed angle rotor while being filtered using an Amicon Ultra-15 (100 kDa MWCO) for 30 minutes at 8° C. Then, the solution was resuspended in 3 mL sterile PBS. This SH-PEG-NHS structure acts as the anti-CD3 antibody linker as the diol group nonspecifically binds to gold.

A 0.2 mg aliquot of antiCD3 antibody with SH-PEG mass in 3 mL was mixed with 1 mL of NPs with anti-HER2 made in the first step. This mixture was spun down in 10 mL sterile PBS. The supernatant was saved for BCA assay, and the remaining precipitate was resuspended again in 10 mL sterile PBS and spun. The supernatant was discarded, and the precipitate resuspended in 1 mL sterile PBS. With the anti-CD3 conjugating to the 3-5 nm elevated nanospheres of gold, it projects out more, allowing for efficient capture of CAR-T cells.

Table 4 shows exemplary components for the nanoparticles described herein.

TABLE 4

| | Exemplary Nanoparticle components | | | |
|---|---|---|---|---|
| Name | Brand name | Mfr. | Cat. No. | Immunogen |
| Anti-CD3 | CD3 antibody | CD3-12 | Bio-Rad | MCA1477 | Synthetic peptide sequence derived from cytoplasmic epitope of CD3 (Glu-Arg-Pro-Pro-Pro-Val-Pro-Asn-Pro-Asp-Tyr-Glu-Pro-Cys) |
| Anti-HEr2 | Herceptin ® (Trastuzumab) 440 mg | Genentech | 440 mg vial | — |
| CD19 | Recombinant Human CD19 Fc Chimera Protein, CF | R&D systems | 9269-CD-050 | — |
| CAR-T cell | CD19 scFv-CD22 scFv-4-1BB-CD3-T2A-RQR8 (Ritiximab suicide switch) | Promab | PM-CAR1050-1M | — | for 35 minutes, activating the attached azides on the NP's and providing a binding site for amines.

A 1 mg sample of DBCO-NHS, 3 mg of anti-HER2 antibody protein, and 2 mL PBS were mixed together and spun overnight at 4° C. 10 mL of buffer was added, and the solution was spun at 3000 RPM in a swing bucket centrifuge while being filtered through an Amicon Ultra-15 100 kDa Example 2

Cell Lines and Cell Culture Media

PC3, SKBR3, and HUVEC cells were obtained from Innoprot. Human prostate carcinoma cell line PC3 (Linterna, P20115, Batch #170913) was cultured in F-12K Medium (Kaighn's Modification of Ham's F-12 Medium) (Gibco), supplemented with 10% heat inactivated fetal bovine serum (FBS; Gibco). Human breast cancer cell line SKBR3 (Linterna, P20129, Batch #120916) and human ovarian cancer cell line SKOV3 (Harper Cancer Research) were cultured in McCoy's 5A Medium (Gibco), supplemented with 10% heat inactivated FBS (Gibco). Human umbilical vein endothelial cells (HUVECs) (TTFLUOR HUVEC cells, P20201, Batch #311018) were cultured in Endothelial Cell Growth Base Media (R&D Systems), supplemented with 2% Endothelial Cell Growth Supplement (R&D Systems). T cells were obtained from Promega. Mock CAR T cells (PM-CAR1000, Lot #110618), CAR T cells (PM-CAR1050, CD19-CD22-4-1BB-CD3z (RQR8 suicide switch), Lot #080219), and T cells (PM-CAR2003, Non-transduced T-cells, healthy donor, Lot #090518) were cocultured in CAR T-Cell Medium (ProMab).

Cell Culture

Human prostate carcinoma cell line PC3 was cultured in F-12K Medium (Kaighn's Modification of Ham's F-12 Medium) (Gibco), supplemented with 10% heat inactivated fetal bovine serum (FBS; Gibco). Human breast cancer cell line SKBR3 and human ovarian cancer cell line SKOV3 (Harper Cancer Research) were cultured in McCoy's 5A Medium (Gibco), supplemented with 10% heat inactivated FBS (Gibco). Human umbilical vein endothelial cells (HUVECs) were cultured in Endothelial Cell Growth Base Media (R&D Systems), supplemented with 2% Endothelial Cell Growth Supplement (R&D Systems.

SKBR3 cell line ($>3 \times 10^6$ cells) was thawed and added to a 15 mL centrifuge tube. 10 mL of McCoy's 5A Medium was added to the tube drop by drop. The tube was centrifuged at 1200 RPM for 5 minutes. Supernatant was aspirated and the cells were resuspended in cell culture media. Cells were equally split into 3 T25 flasks and cell culture media was added. Cell culture media was changed every day for the first three days. At 80-90% confluency, cells were passaged into a T75 flask. Cell culture media was changed about every two days. At around 70% confluency, cells were split into 4 T75 flasks and media was changed the next day. At around 50-60% confluency, cell culture media was aspirated, and the flask washed with 10 mL sterile phosphate buffered saline (PBS). PBS was aspirated and 1 mL trypsin-EDTA was added. Cells were put into a 37° C., 5% $CO_2$ incubator for 5 minutes. The flask was tapped to detach the cells from the bottom of the flask. 9 mL cell culture media was added to the flask. Trypsin-EDTA and cell culture media containing detached cells was transferred to a 15 mL centrifuge tube and centrifuged at 1200 RPM for 5 minutes. Supernatant was discarded and pellet was resuspended in 4 mL cell culture media. PC3 and SKOV3 cells followed the same protocol. HUVEC cells were thawed and followed the same protocol but were immediately added to 8 well chamber slides rather than in cell culture flasks.

CAR-T, Mock CAR-T, T Cells

CAR-T cells ($1 \times 10^6$ cells/vial), mock CAR-T cells ($1 \times 10^6$ cells/vial), and T cells ($2 \times 10^6$ cells/vial) were purchased from Promega. Cells were thawed and resuspended in 10 mL CAR T-cell Medium (ProMab) in a 15 mL centrifuge tube. Tubes were centrifuged at 1200 RPM for 5 minutes, supernatant discarded, and pellet was resuspended in 3.5 mL T cell media.

Fluorescent Tumor Killing Assay

The fluorescent tumor killing assay took four days to complete. Tumor cell lines were plated on 8 8-well chamber slides. A volume of 400 μL media/well was maintained throughout the four days. Anti-CD3/anti-HER2 bi-specific NPs and anti-HER2 NPs were then added to the wells.

Afterwards, three different types of T cells were added to the wells: CAR-T cells, Mock CAR-T cells, and T cells. To activate the CAR-T cells, CD19 was then added to each well in three varying concentrations: high, medium, and low. Finally, the cells were fixed and imaged using fluorescent microscopy.

Cell Plating

Cell lines were maintained as stated above in T75 flasks. Prior to plating the cells in chamber slides, one 50-60% confluency flask was trypsinized and centrifuged as described above, the supernatant was aspirated, and the cell pellet resuspended in 4 mL of media. 10 μL of cell solution was pipetted onto a haemocytometer and cells were counted. Each cell line was diluted in separate 50 mL centrifuge tubes. 400 μL of the cell solution were pipetted into each well of an 8 well chamber slide (approximately 15,000 cells/well). Slides were then incubated for 24 hrs at 37° C., 5% $CO_2$.

Nanoparticle Addition

After 24 hrs, each cell line was around 30% confluent. Cell culture media from each well was carefully aspirated and 400 μL cell culture media was added to each well. Tissue culture hood light was turned off to preserve RITC-SiO$_2$-Au NP fluorescence. 6.8 μL anti-CD3/anti-HER2 NPs was added to slides 1-7: wells 1, 2, 3, 5, 6, 7, 6.8 μL anti-CD3/anti-HER2 NPs was added to slide 8: wells 3, 4, 5, 6, 7, 8. 6.8 μL anti-HER2 NPs was added to slides 1-7: wells 4 and 8. Slides were covered in aluminum then incubated for 24 hrs at 37° C., 5% $CO_2$.

T Cell Addition

CAR-T cells ($1 \times 10^6$ cells/vial), mock CAR-T cells ($1 \times 10^6$ cells/vial), and T cells ($2 \times 10^6$ cells/vial) were thawed and prepared as described above. T cells were centrifuged and resuspended in 3.5 mL T cell media as described above. Tissue culture hood light was turned off and T cells were added to the slides as described in (Table 5). Slides were again covered in aluminum foil then incubated for 24 hrs at 37° C., 5% $CO_2$.

TABLE 5

| | T-Cell Addition to Chamber Slides | |
| --- | --- | --- |
| Slide | Wells | T-Cells (in μL) |
| 1 | 1--8 | 40 CAR-T |
| 2 | 1--4 | 40 CAR-T |
| | 5--8 | 20 CAR-T |
| 3 | 1--8 | 20 CAR-T |
| 4 | 1--4 | 40 CAR-T |
| | 5--8 | 20 CAR-T |
| 5 | 1--8 | 40 T-cell |
| 6 | 1--8 | 40 mock CAR-T |
| 7 | 1--4 | 50 T-cell |
| | 5--8 | 50 mock CAR-T |
| 8 | 5--6 | 40 mock CAR-T |
| | 7--8 | 40 T-cell |

CD19 Addition

After incubating for 24 hrs, media was carefully aspirated from each well. 350 μL cell culture media was added to each well. CD19 was prepared by diluting a mass CD19 stock ($5 \times 10^{-8}$ g/μL) to $5 \times 10^{-12}$ g/μL in sterile PBS. Tissue culture hood light was turned off and the diluted CD19 was added to the wells in three concentrations High (18 μL), Medium (10 μL), and Low (5 μL). Slides were covered with aluminum foil then incubated for 24 hrs at 37° C., 5% $CO_2$.

Fixing Cells

After 24 hrs, media from each well was transferred to individual vials for ELISA. 200 μL 4% paraformaldehyde (PFA) was added to each well and was let to sit for 10 minutes under aluminum foil to block the light, preserving fluorescent qualities. After 10 minutes, PFA was removed and 400 μL PBS was added to each well. Slides were again covered with aluminum foil then imaged using a fluorescent microscope.

Fluorescent Microscopy

PC3, SKBR3, and SKOV3 cell lines were analyzed using a 10× objective on a TE2000 inverted microscope (Nikon). Bright field (16-bit-binning 2×2, 40 ms exposure), red channel (16-bit-binning 2×2, 300 ms exposure), and green channel (16-bit-binning 2×2, 300 ms exposure) images were obtained by a Hamamatsu CMOS camera controlled by NIS-Elements BR 413.04 64-bit software (Nikon). Data was further processed using Fiji/ImageJ (National Institutes of Health).

HUVEC cell line was analyzed using a 10× objective and 0.25 N.A. on a DMi8 Inverted Fluorescent Microscope (Leica). Bright field, N21 TexasRed (Red channel), and GFP-EN (GFP-Green channel) (300 ms exposure) images were obtained by a sCMOS camera controlled by Leica Application Suite (LAS X) software (Leica). Data was further processed using Fiji/ImageJ (National Institutes of Health).

ELISA Tests

Three different ELISA tests, Human Granzyme B, Perforin and Human IL-2, were completed in order to measure the amount of specified cytokine is present in the samples.

Human IL-2 ELISA

The Human IL-2 ELISA kit was purchased from Bio-Legend. The plate was first coated with 100 μL capture antibody, sealed, and incubated at 2-8° C. overnight. Reagents were brought to room temperature and 1× assay diluent A was added to each well to block non-specific binding. The plate was sealed and incubated at room temperature for 1 hour on a plate shaker. The samples and standard were added to each well and incubated at room temperature for 2 hours with shaking. Detection antibody was added to each well then incubated at room temperature for 1 hour with shaking. Avidin-HRP solution was added and the plate was incubated at room temperature for 30 minutes with shaking. TMB substrate was added and then incubated in the dark for 30 minutes. The positive wells turned blue. Stop solution was added to stop the reaction causing positive wells to turn from blue to yellow. The absorbance was measured at 450 nm within 15 minutes of stopping the reaction.

Human Granzyme B and Perforin ELISA

The Human Granzyme B ELISA kit was purchased from MabTech. These plates were already coated with the capture antibody. Samples and standard were added, the incubated for 2 hours at room temperature. Detection antibody was then added, and the plate was incubated at room temperature for 1 hour. Streptavidin-HRP was added and incubated at room temperature for 1 hour. TMB substrate was added and the plate was incubated at room temperature in the dark for 15 minutes. Stop solution was added and the absorbance was measured at 450 nm within 15 minutes of stopping the reaction.

The Perforin ELISA was performed using a similar procedure as used for the human granzyme B ELISA.

Example 3

Structural Similarity of Phage-Mimicking Nanoparticles to Bacteriophages

Figures 3A, 3B, 3C, 3D:
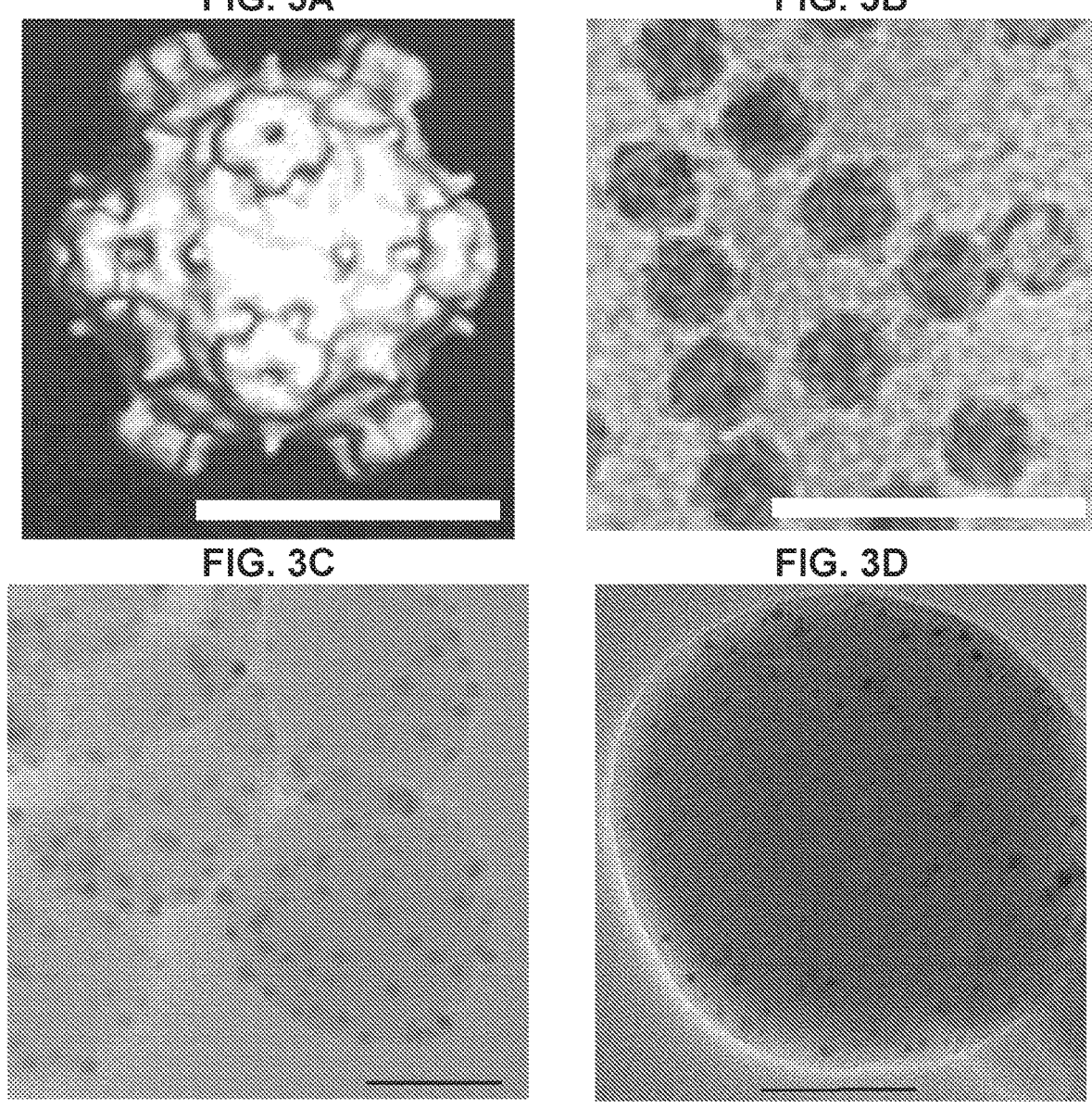
FIG. 3A-B show a rendering and a micrograph of a procapsid particle of bacteriophage φX174 presented as (FIG. 3A) a surface-rendered image (FIG. 3A; scale bar: 20 nm) from cryo-electron microscopy images (HRTEM) (FIG. 3B; scale bar: 100 nm) (both images reproduced with permission from Ilag et al., *Structure* 3 (4): 353-363 (1995)).
FIG. 3C-D show micrographs of small and large nanoparticles with the gold particles visible as dark spheres on the surface of the silicon dioxide cores.
Figure 3E:
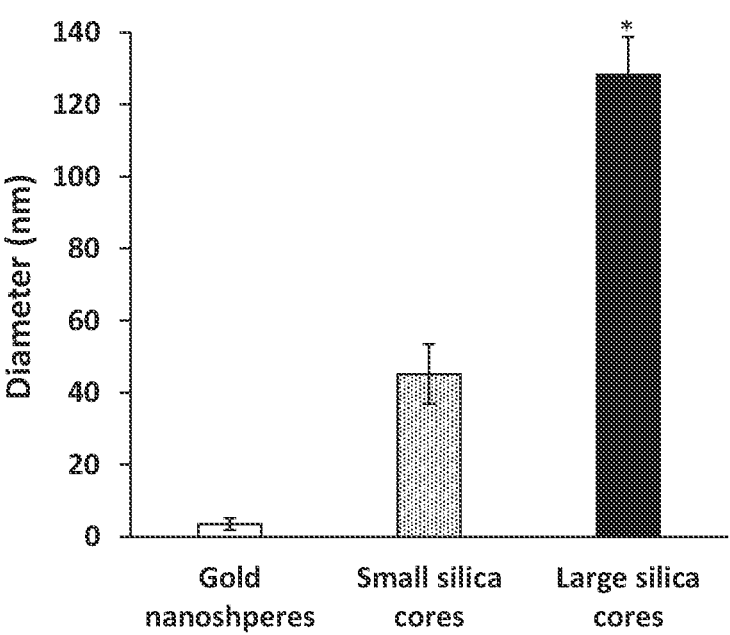
FIG. 3E shows bar graphs of the mean diameters of the gold nanospheres and silicon dioxide cores.
Figure 3F:
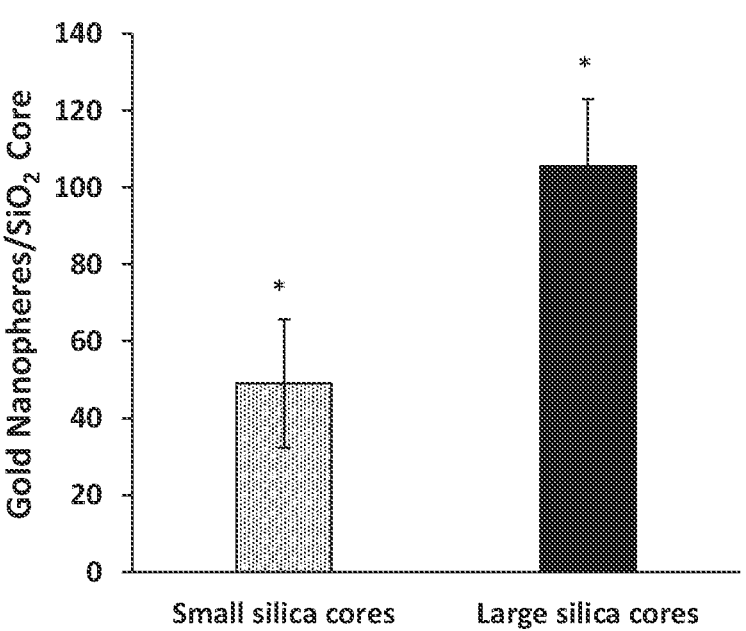
FIG. 3F shows the average number of gold nanospheres on the 45 nm or 130 nm silicon dioxide cores. * $P \leq 0.01$ (t- and f-test).
Figures 4A, 4B, 4C, 4D, 4E, 4F, 4G, 4H:
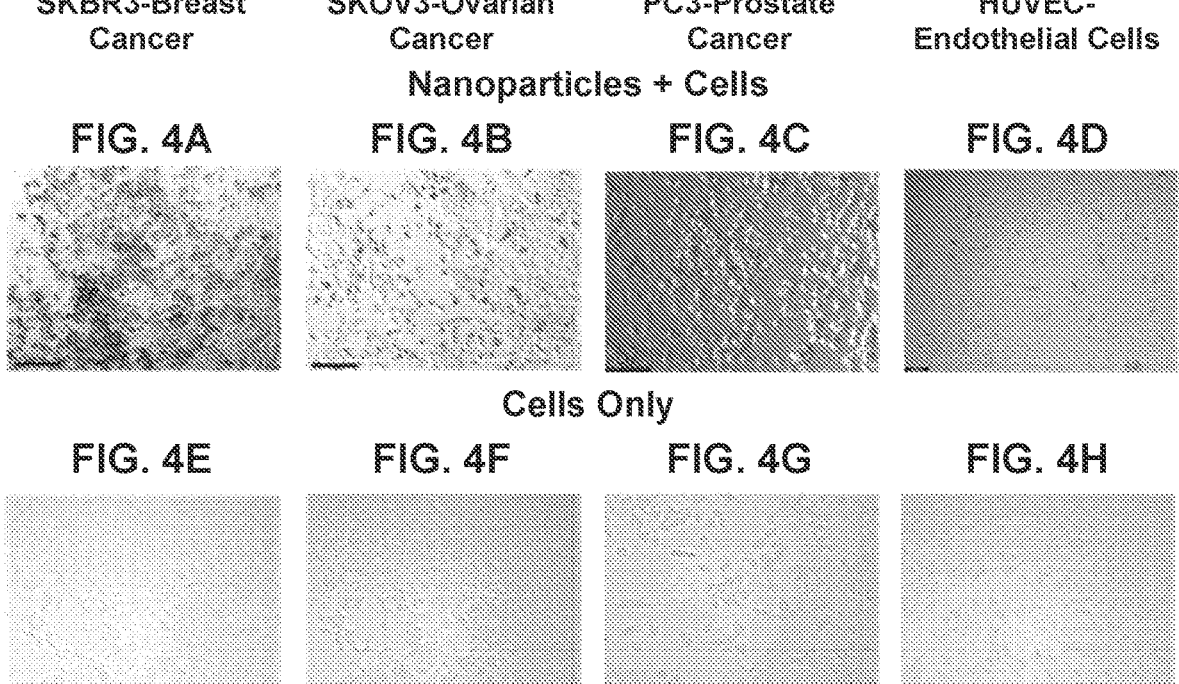
FIG. 4A-H show bright field microscopy images of tested cells added with bridge NPs compared with control images of the cell alone. The anti-HER2 component of the bridge nanoparticles bound to all cancer cells, with the highest binding density to HER2 overexpressing SKBR3 as expected. The binding density of the bridge nanoparticles from high-to-low cancer cells was SKBR3>SKOV3>PC3. There was insignificant binding to the control HUVEC cells.

For a visual comparison, FIGS. 3A and B show the structure of a tailless phage (the example of bacteriophage φX174) that acted as a template for the design of the nanoparticles. TEM image analysis revealed that the small and large $SiO_2$ cores had diameters of approximately 45±8.25 nm and were covered with 3.5±1.57 nm gold-nanospheres (FIG. 3C-E). The amount of gold nanospheres covering the phage-mimicking ANPs ~50 for the 45 nm core size (FIG. 3F).

In general, the size of the smaller phage-mimicking ANPs (45 nm) relates better to the capsid sizes of tailless bacteriophages than that of the larger 130 nm phage-mimicking ANPs. Both the 45 nm and 130 nm core sizes carry more gold nanospheres per unit area in comparison to the number of protein turrets on the heads of the bacteriophage's capsids (~4× and 8× higher, respectively). Regardless, the 2.02 nm interspacing between the gold nanospheres of the small 45 nm phage-mimicking ANPs is at least 4× smaller than the geometrically consistent distance between the protein-turrets covering the surface of the phage capsids.

Interestingly, the bacteriophage SpV4 possesses a surface density of protein turrets ($0.0068 \, nm^{-2}$) that is 88% similar to the surface density of gold nanospheres ($0.0077 \, nm^{-2}$) on small 45 nm phage-mimicking ANPs. The SpV4 bacteriophage belongs to the viral family of Microviridae which are small (25-27 nm), tailless bacteriophages. One genus of this family is named Chlamydiamicrovirus and as the name suggests it infects various species of the obligate intracellular and pathogenic *Chlamydia*. Bacteriophages of the genus Chlamydiamicrovirus are known to initiate infection of the bacterial host cell by pilus-mediated adsorption, which is dependent on the external bacteriophage structure as well as the host cell receptors. For the cell experiments only nanoparticles with core-diameters between 45 nm to 60 nm were used.

Bioconjugation of Antibodies to Bridge Nanoparticles

The bare surface of the silica core of the bridge nanoparticles presents amine functional groups ($—NH_2$) due to APTES being included in the synthesis protocol. The amine groups are highly useful for further functionalization through the formation of amide bonds or bonds with isothiocyanate groups. The azide groups were conjugated to the amine groups using N-hydroxysuccinimide-azide (NHS-Azide). The NHS component linked the azide group to the amine groups on the silica cores by forming an amide bond. Separately the anti-HER2 (Herceptin) antibody was conjugated to DBCO-NHS. DBCO is the complementary CLICK reagent to azide for copper-free CLICK chemistry. This method of conjugation yielded 90.47% conjugation efficiency as determined by BCA assay. This translated to 0.095328 μg of anti-HER2 per 1 μg of NPs.

In the case of anti-CD3, the amine groups of the Fc region were conjugated at pH 7.4 with NHS-PEG(200 Da)-thiol. The NHS ester formed an amide bond with the amine groups on the anti-CD3. Then the antibodies with the NHS-PEG (200 Da)-thiol linkers were separated out from the unbound NHS-PEG(200 Da)-thiol by using a 100 kDa MWCO centrifugal filter. The anti-CD3 conjugated with the NHS-PEG (200 Da)-thiol linkers were simply mixed with the anti-HER2 bound bridge nanoparticles. The thiol groups chemisorbed rapidly onto the bare gold nanoparticles on the silica core. In this manner the bridge nanoparticles had tumor binding ani-HER2 and uCAR-T binding anti-CD3 bound on the same nanoparticle. BCA assay showed a protein loading of 0.0067 μg of antiCD3 per 1 microgram of NPs, which was near 100% conjugation efficiency.

Bridge Nanoparticles Binding to Three Different HER2 Expressing Cancer Cells and Control Cells The bridge nanoparticles were incubated with the cells for 24 h after which the cell culture media was gently aspirated and replaced with fresh media so that all the unbound bridge nanoparticles were removed from the cell culture wells. The anti-HER2 component of the bridge nanoparticles bound to all cancer cells, with the highest binding density to HER2 overexpressing SKBR3 as expected. The binding density of the bridge nanoparticles from high-to-low to cancer cells was SKBR3>SKOV3>PC3. There was insignificant binding to control HUVEC cells. Breast cancer cell SKBR3 had maximum staining, showing that it had the highest surface density of HER2. This is expected as HER2 is known to be abundant in the plasma membrane of SKBR3 cells. There was also significant binding of bridge nanoparticles to SKOV3 under visual inspection. PC3 had ~30% of cells with high concentrations of bridge nanoparticles bound to the surface. PC3 are not known to uniformly overexpress HER2. Nearly 100% of the SKBR3 cells were stained in the field-of-view. 65-72% of SKOV3 cells were stained as well. Only ~26% of the PC3 cells were stained by bridge nanoparticles in the field of view. Even with such low percentage of PC3 cells being bound by the bridge nanoparticles, nearly 33% of PC3 cells were killed by the uCAR-T cells. Thus, the binding pattern of bridge nanoparticle to certain PC3 cells only aligns well with peer-reviewed data about HER2 expression levels on PC3 cells. But the bridge nanoparticles were still able to redirect uCAR-T cells to the PC3 cells and achieve significant cancer cell death. With the control cells, the bridge nanoparticles were found to outline certain HUVEC cells. This would indicate an insignificant level of non-specific binding to the extra-cellular matrix of the HUVEC cells. See FIG. 4A-H uCAR-T Cells Anchored to Bridge Nanoparticles Binding to HER2 Expressing Cancer Cells and Control Cells The uCAR-T cells were incubated with the test samples (cells previously incubated with the dual-antibody bridge nanoparticles) and control samples (e.g., cells that were incubated with single antibody nanoparticles, null antibody nanoparticles or no nanoparticles) for 24 hours. After 24 hours, the cell culture media was gently aspirated and replaced with fresh media so that all the unbound uCAR-T cells were removed from the cell culture wells. uCAR-T cells were immunostained by using blue-fluorescent Cy3-anti-CD3. The blue immunostaining in the images (FIG. 5A-H) shows that bridge NP's successively anchored the uCAR-T cells as shown in the concept model (FIG. 1). The cells frames analyzed were 150 μm×200 μm with 15,000 cells seeded per well. Significantly more uCAR-T cells were bound to cancer cells than HUVEC cells. Interestingly although the uCAR-T to cancer cells or control cells ratio was 1:1, after accounting for test cells division, immunostaining did not demonstrate a 1:1 binding of uCAR-T cells to test cells although this did not affect the uCAR-T cells ability to kill cancer cells shown below. See FIG. 5A-H.

Total Cell Viability Post-uCAR-T Activation Using CD19

Determining Degree of Apoptosis by Staining for BAD Proteins in HER2 Expressing Cancer Cells and Control Cells The BCL2 associated agonist of cell death (BAD) protein is a pro-apoptotic member of the Bcl-2 gene family which is involved in initiating apoptosis. BAD is a member of the BH3-only family, a subfamily of the Bcl-2 family.

Bax/Bak are believed to initiate apoptosis by forming a pore in the mitochondrial outer membrane that allows cytochrome c to escape into the cytoplasm and activate the pro-apoptotic caspase cascade. The anti-apoptotic Bcl-2 and Bcl-xL proteins inhibit cytochrome c release through the mitochondrial pore and also inhibit activation of the cytoplasmic caspase cascade by cytochrome c.

Dephosphorylated BAD forms a heterodimer with Bcl-2 and Bcl-xL, inactivating them and thus allowing Bax/Bak-triggered apoptosis. When BAD is phosphorylated by Akt/protein kinase B (triggered by PIP3), it forms the BAD-(14-3-3) protein heterodimer. This leaves Bcl-2 free to inhibit Bax-triggered apoptosisBAD phosphorylation is thus anti-apoptotic, and BAD dephosphorylation (e.g., by $Ca^{2+}$-stimulated Calcineurin) is pro-apoptotic.

Figures 6A, 6B, 6C, 6D, 6E, 6F, 6G, 6H:
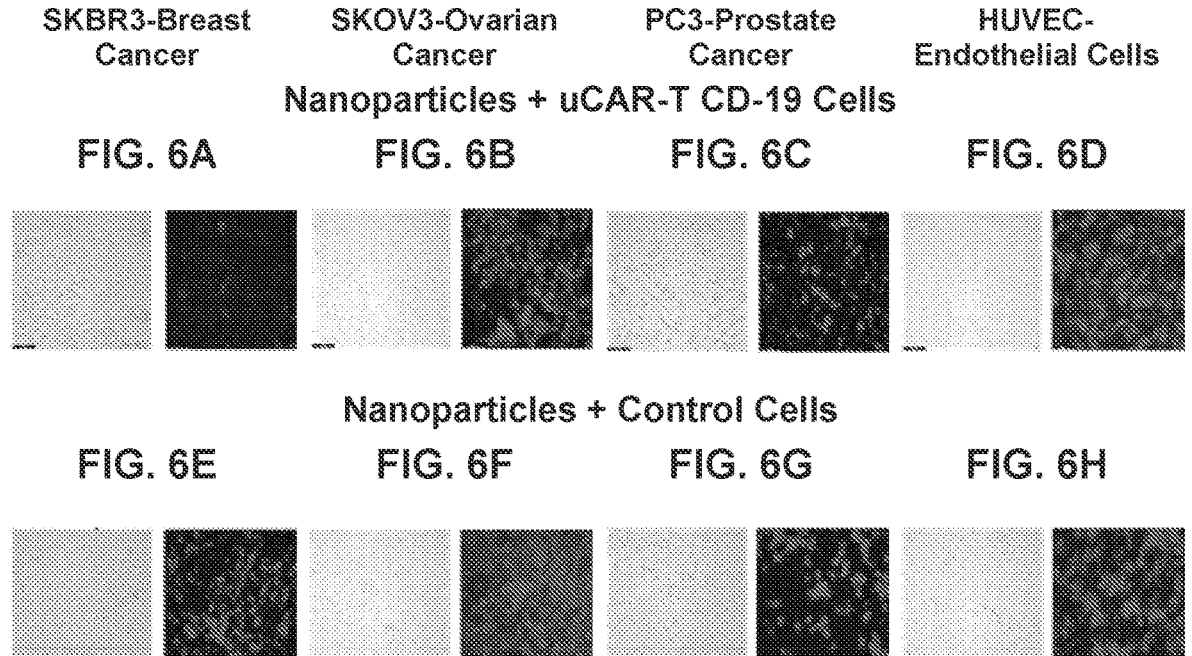
FIG. 6A-H show bright field microscopy images (grayscale) and fluorescent microscopy images (blue and black) of apoptosis assay with immunostaining of phosphorylated BAD proteins. The tested cells were added with bridge NPs and uCAR-T-CD-19 and compared with images of tested cells added with only bridge NPs. Immunostaining for phosphorylated BAD proteins stained non-apoptotic cells. The percent population of apoptotic and non-apoptotic cells was then calculated in comparison to the control population for each cell line.

The cells were stained for phosphorylated BAD to determine non-apoptotic cells and the percent apoptotic cells were determined. SKBR3 had the most apoptotic cells. FIG. 6A.

Cell Viability Levels by Assessing GFP Expression Levels in HER2 Expressing Cancer Cells FIG. 7A-H show the fluorescence viability assay in live cells. A drop in fluorescence intensity from GFP corresponded to an increase in cell necrosis. The differences in fluorescence intensity was quantified and normalized against the control for each cell line.

At the endpoint of necrosis, there is leakage and degradation of the intracellular content resulting from the perforation of the membrane, allowing GFP's to leak out of the cell. There can also be chemical changes in the cell affecting the activation of the GFP's. These events involving cell necrosis correspond to GFP's fluorescence not being able to be detected. In apoptotic cells, GFP fluorescence can still be detected as the apoptotic cells remain intact until late phases. GFP fluorescence intensity is also shown to be in correlation with transcriptional activity. See FIG. 8A-M, Table 6.

Figures 7A, 7B, 7C, 7D, 7E, 7F, 7G, 7H:
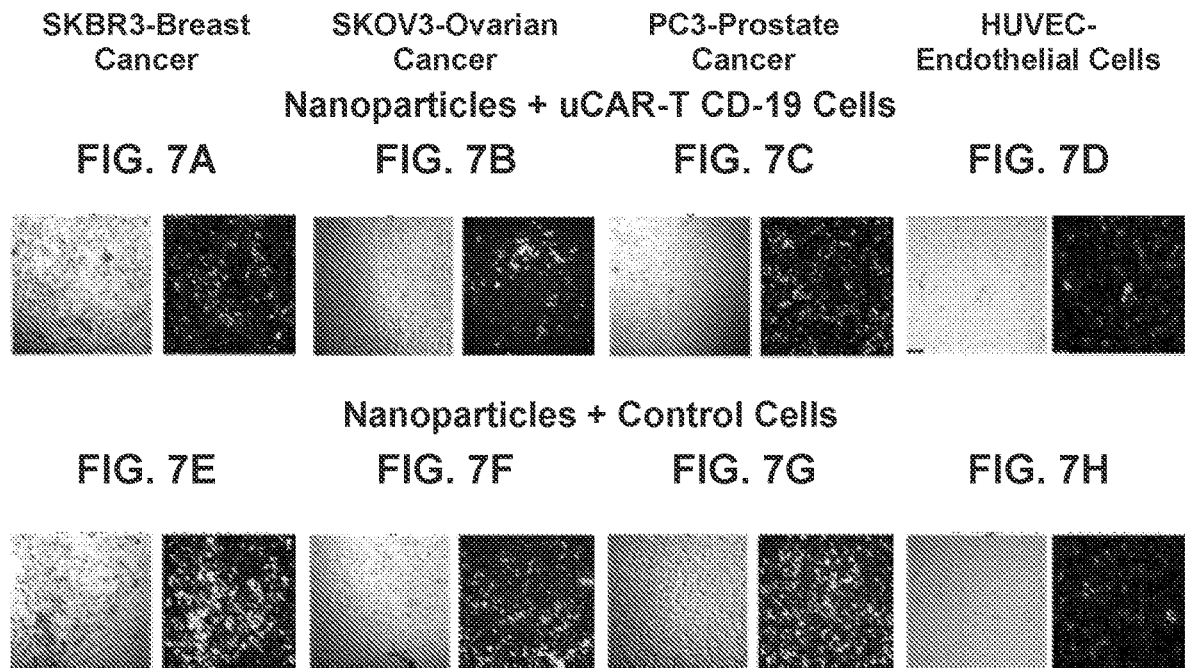
FIG. 7A-H shows photomicrographs illustrating cell death after contact with uCAR-T cells and bridge nanoparticles. A decrease in GFP fluorescence intensity corresponds to an increase in cell necrosis. The differences in fluorescence intensity were quantified and normalized against the control for each cell line.

SKOV3 exhibited the highest sensitivity to CD19 activation of uCAR-T cells (FIG. 7B). PC3 exhibited CD19 dose dependent drop in viability with highest dose of CD19 resulting in maximum cell death.

The results of the apoptosis assay and the cell viability assays were quantified and denoted as bar graphs in FIG. 8A-M. Apoptotic cells and necrotic cells were combined to determine total non-viable cell population. The total non-viable cell population was then used to determine effectiveness of the Bridge nanoparticles in redirecting an off-the-shelf uCAR-T cell against three different cancer cells of solid origin in FIG. 8A-L, Table 6, FIG. 8M.

TABLE 6

Total Viable Cells as a Function of Cell Line and uCAR-T Activator Dose

| | uCAR-T Activator Dose | | | |
| Cell lines | CD19 High | CD19 Medium | CD19 Low | Control (no CD19) |
| --- | --- | --- | --- | --- |
| SKBR3-breast cancer | 24.7 ± 5.5%* | 29.1 ± 10.7%* | 36.7 ± 7.7%* | 100% |
| SKOV3-ovarian cancer cells | 7.2 ± 9%* | 3.1 ± 8%* | 37.5 ± 8%* | 100% |
| PC3-prostate cancer cells | 67.1 ± 10.9%* | 81.6 ± 6.8%* | 94.5 ± 7.6% | 100% |
| HUVEC-control cells | 100% | 80.5 ± 9.2% | 100% | 100% |

*Statistically significant cell death compared to the control groups. Significance was determined using a paired t-test with $\alpha = 0.05$.

Figures 8A, 8B, 8C, 8D, 8E, 8F, 8G, 8H, 8I, 8J, 8K, 8L:
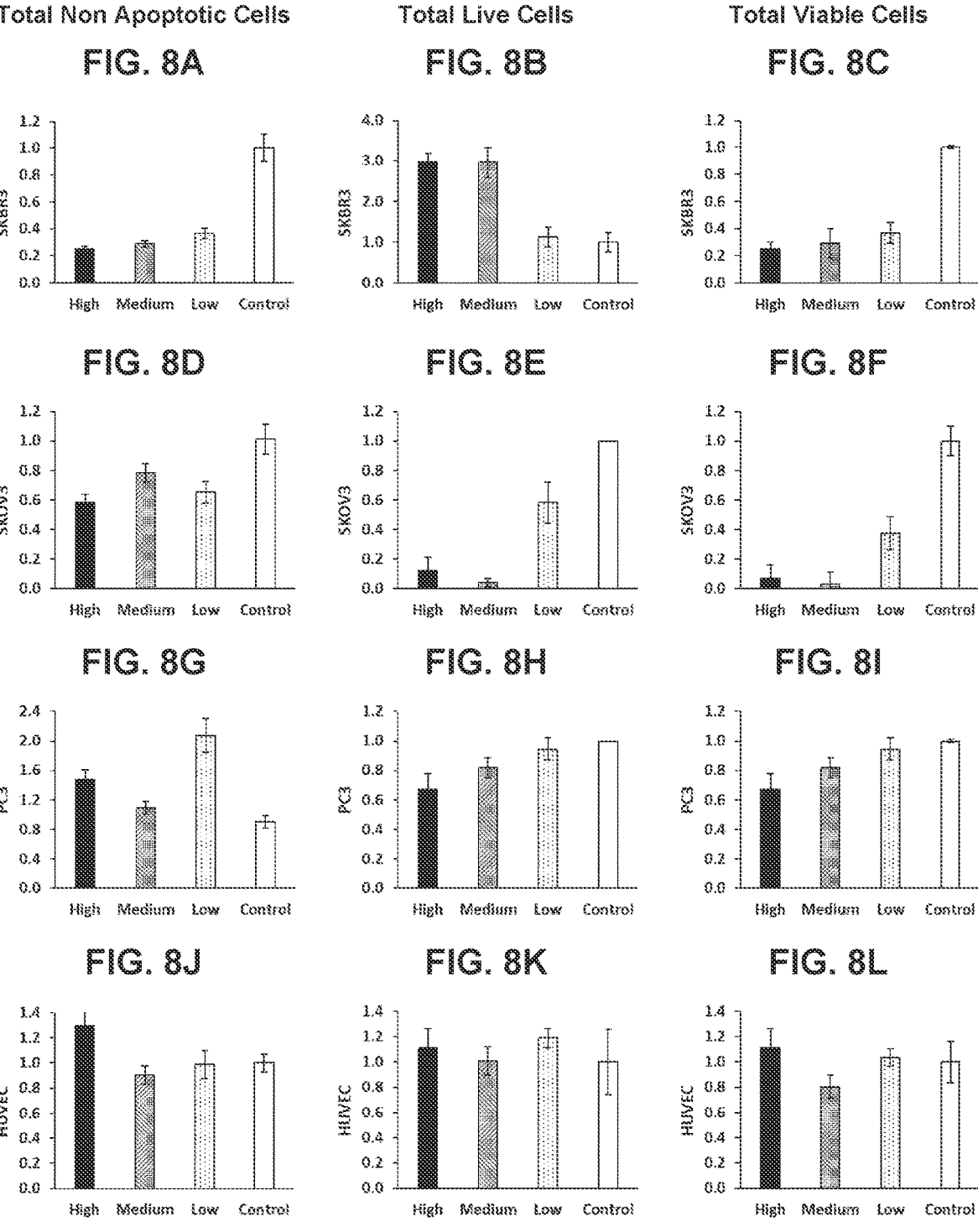
FIG. 8A-M show bar graphs representing the total viable cells from the apoptosis and viability assays after contacting cells with uCAR-T cells and bridge nanoparticles and activation with various concentrations of CD19 activator. The CD19 concentrations were varied from 0.25 pg/µL (High); 0.14 pg/µL (Medium); and 0.07 pg/µL (Low). The total viable cells were calculated from the assays for apoptosis and cell viability, for test and control groups. The test groups were the different CD19 dosages used to activate the uCAR-T cells cytotoxic activity.
Figure 8M:
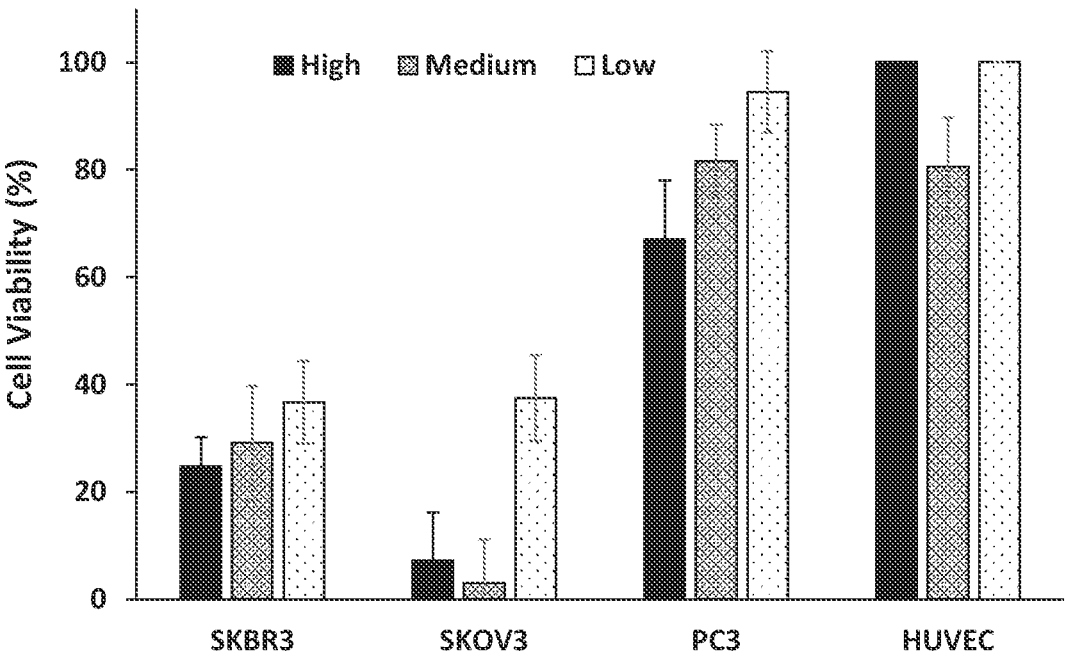

Table 6 and FIG. 8M show that there is significant cancer cell death in response to higher activation of uCAR-T compared to controls. SKBR3 and SKOV3 cancer cells responded substantially better to the uCAR-T's than the PC3 prostate cancer cells. There was insignificant cell death in the HUVEC control cells at all uCAR-T dosages.

There is significant cancer cell death in response to higher activation of uCAR-T compared to control groups. SKBR3 and SKOV3 cancer cells responded substantially greater to the uCAR-T's than the PC3 prostate cancer cell. There was no significant cell death in the HUVEC control cells at all uCAR-T dosages. In SKBR3 (Breast cancer) cells test samples all doses of CD19 significantly reduced cancer viability. In SKBR3, total cell viability post-CD19 activation of uCAR-T cells was between 24.7% to 36.7%. In SKOV3 (ovarian cancer) cells, test samples all doses of CD19 significantly reduced cancer cell viability. In SKBR3, total cell viability post-CD19 activation of uCAR-T cells was between 3.1% to 37.5%. In PC3 (prostate cancer) cells test samples only CD19 high and CD19 medium doses significantly reduced cancer viability. In PC3 cells, a significant difference in total cell viability post-CD19 activation of uCAR-T cells was between 67.1% to 81.6%. In HUVEC (control) cells there was no effect on viability which indicated specificity of the bridge nanoparticles to the cancer cells. The quantitative results of cell-viability are listed in Table 6; data from Table 6 is presented in FIG. 8M.

Determining Levels of Cytotoxic Cytokine Release from CD19 Activated uCAR-T Cells Granzyme B (GrB) is a serine protease most commonly found in the granules of natural killer cells (NK cells) and cytotoxic T cells. Other cytotoxic cytokines tested for were perforin and Interleukin-6 (IL-6).

Experiments were performed to determine whether there was a dose dependent release of cytokines from uCAR-T cells. In addition, the ability to control cytokine concentration was evaluated as a means to mitigate or avoid cytokine release syndrome (CRS) that is commonly seen in immunotherapy. CRS though manageable by treating for symptoms, it has been known to lead to permanent organ damage or even death. The ability to control the concentration of cytokines released from uCAR-T cells was evaluated using two methods:

Method 1 (FIG. 9A-9C): The concentrations of CD19 was varied from 0.25 pg/μL (CD19 High); 0.14 pg/μL (CD19 Medium); and 0.07 pg/L (CD19 Low). The ratio of uCAR-T cells to cancer cells was 1:1.

Method 2 (FIG. 9D-9F): The concentration of uCAR-T was lowered such that the ratio of cancer cells to uCAR-T cells was 2:1. The concentrations of CD19 was varied from 0.25 pg/μL (CD19 High); 0.14 pg/μL (CD19 Medium); and 0.07 pg/μL (CD19 Low) as in Method 1.

Figure 9A:
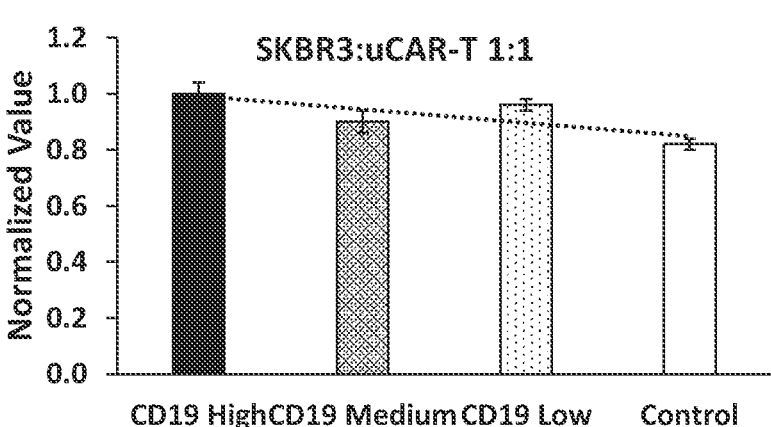
FIG. 9A-F show bar graphs representing ELISA assays detecting Granzyme-B after activation with CD19. The CD19 concentrations were varied from 0.25 pg/µL (High); 0.14 pg/µL (Medium); and 0.07 pg/µL (Low).
Figure 9B:
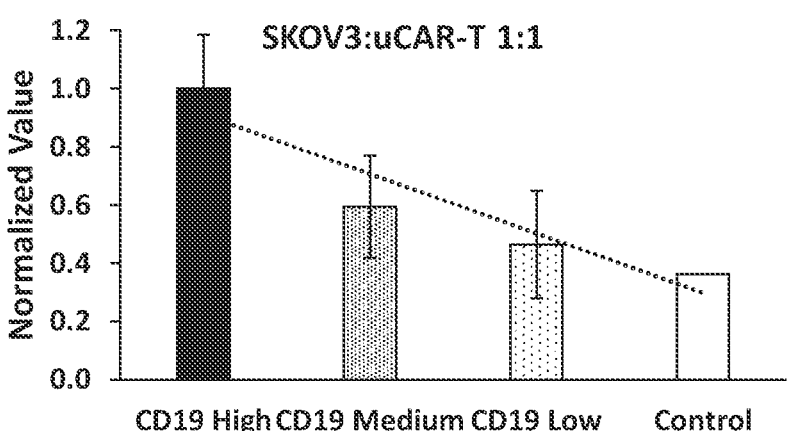
Figure 9C:
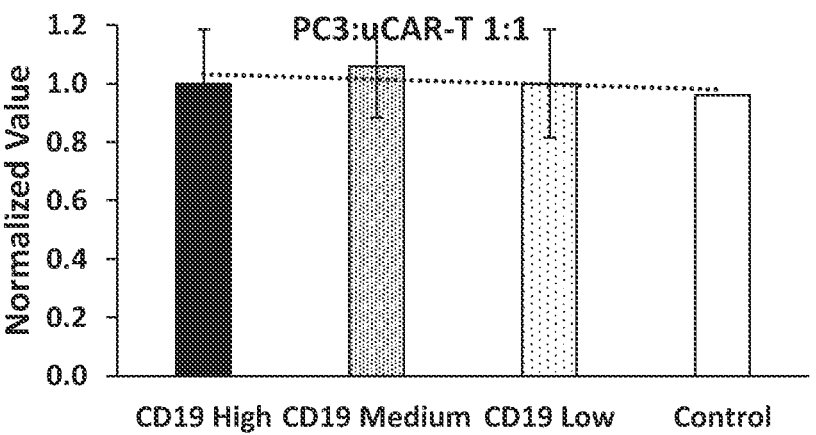
Figure 9D:
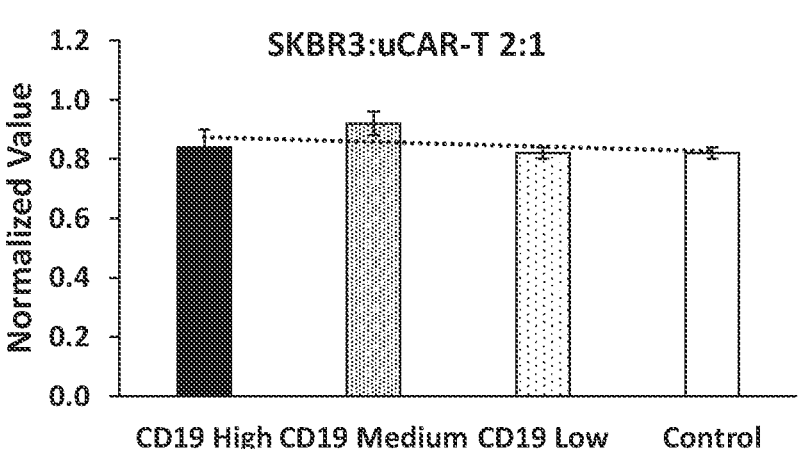
Figure 9E:
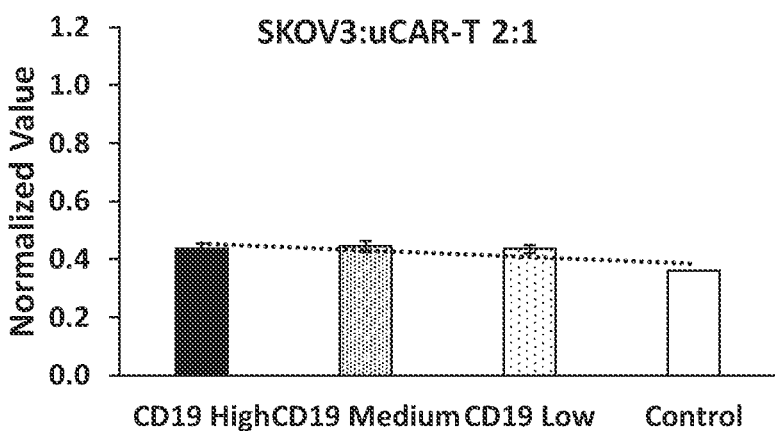
Figure 9F:
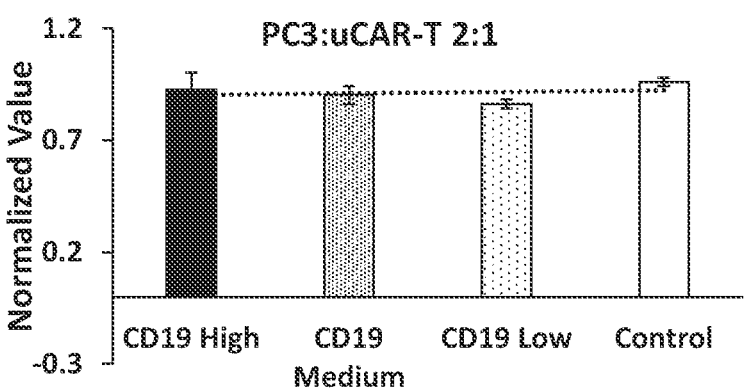
Figure 10A:
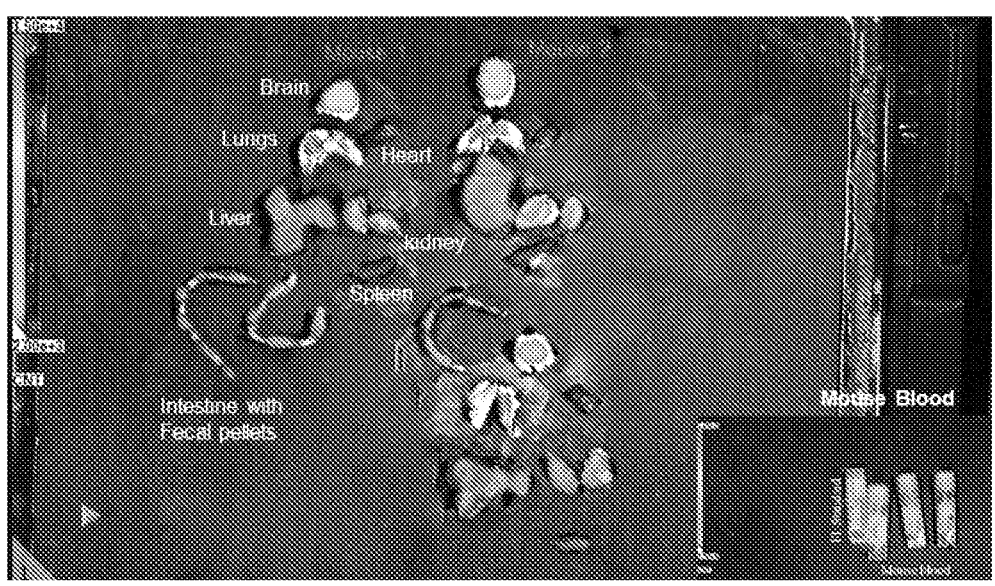
FIG. 10A-D show ex vivo imaging of the biodistribution of AF750 tagged bridge nanoparticles without antibodies at various time points.
Figure 10B:
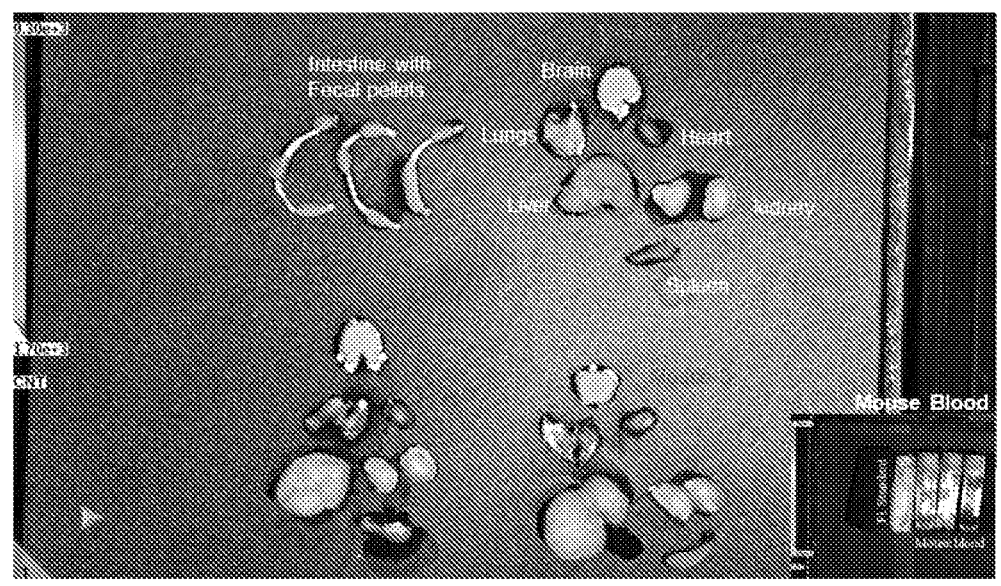
Figure 10C:
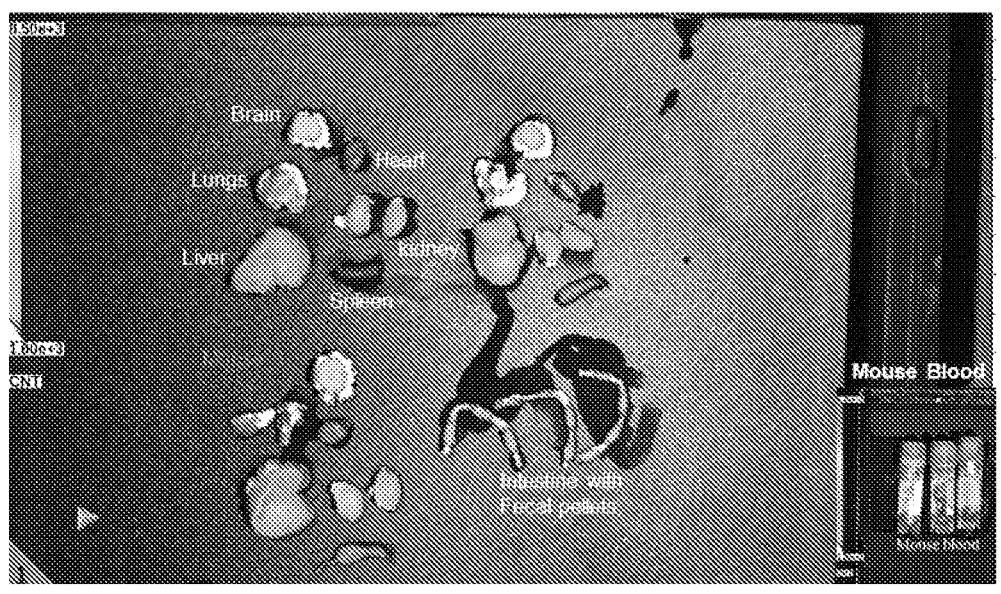
Figure 10D:
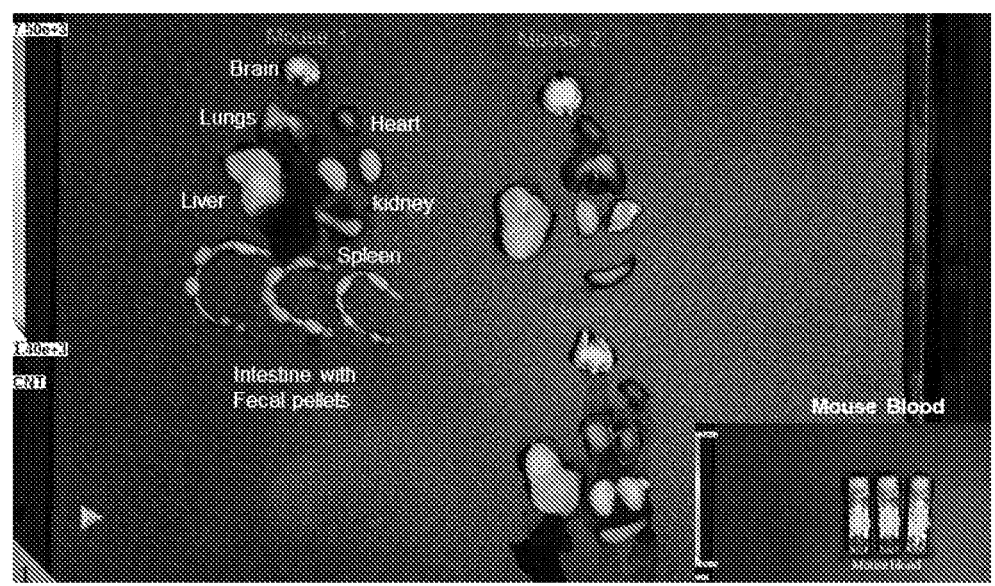
Figure 11:
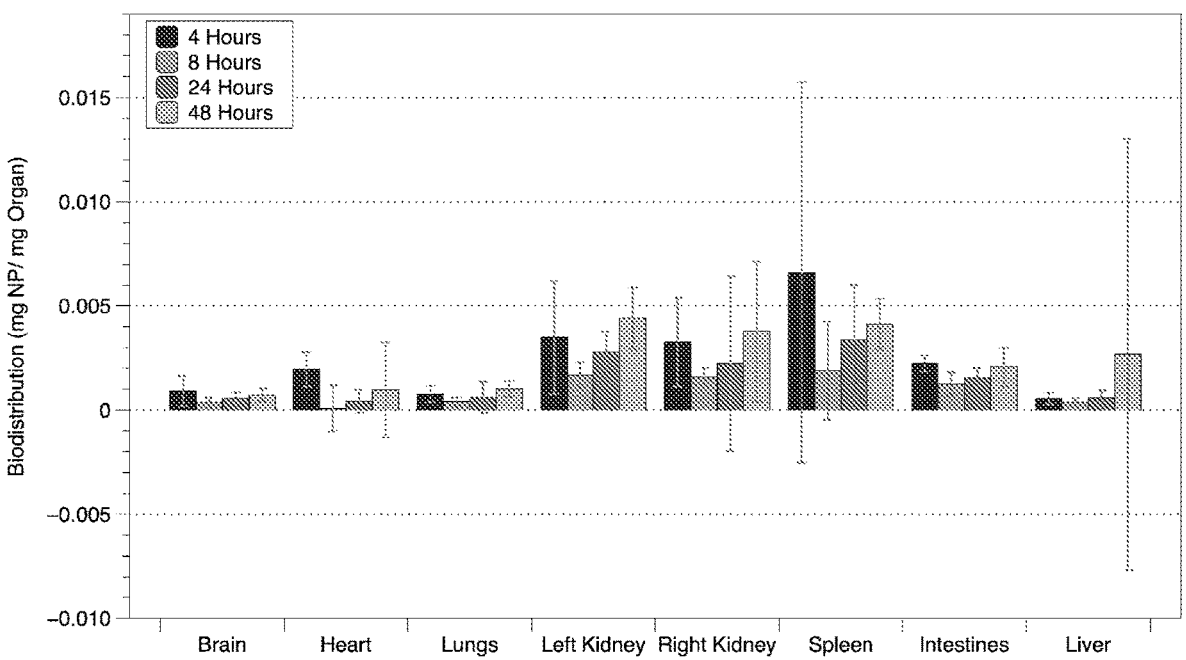
FIG. 11 shows the tissue biodistribution of AF750 tagged bridge nanoparticles without antibodies.
Figure 12A:
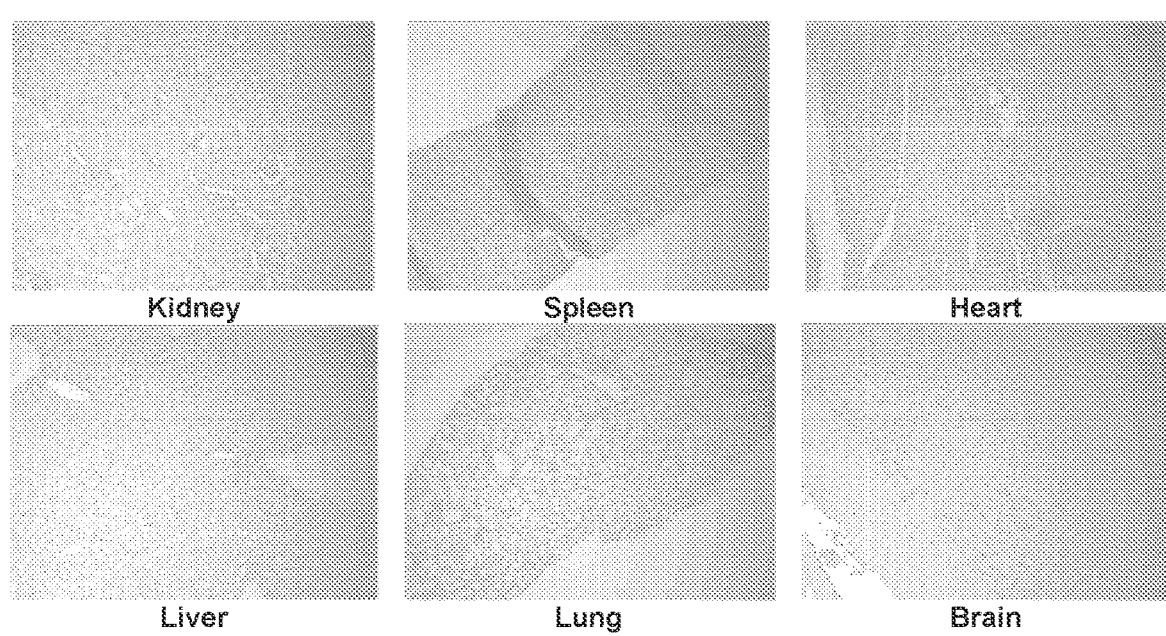
FIG. 12A-D show histology analysis of H&E staining of mouse organs (kidney, spleen, heart, liver, lung, brain) at various time points.
Figure 12B:
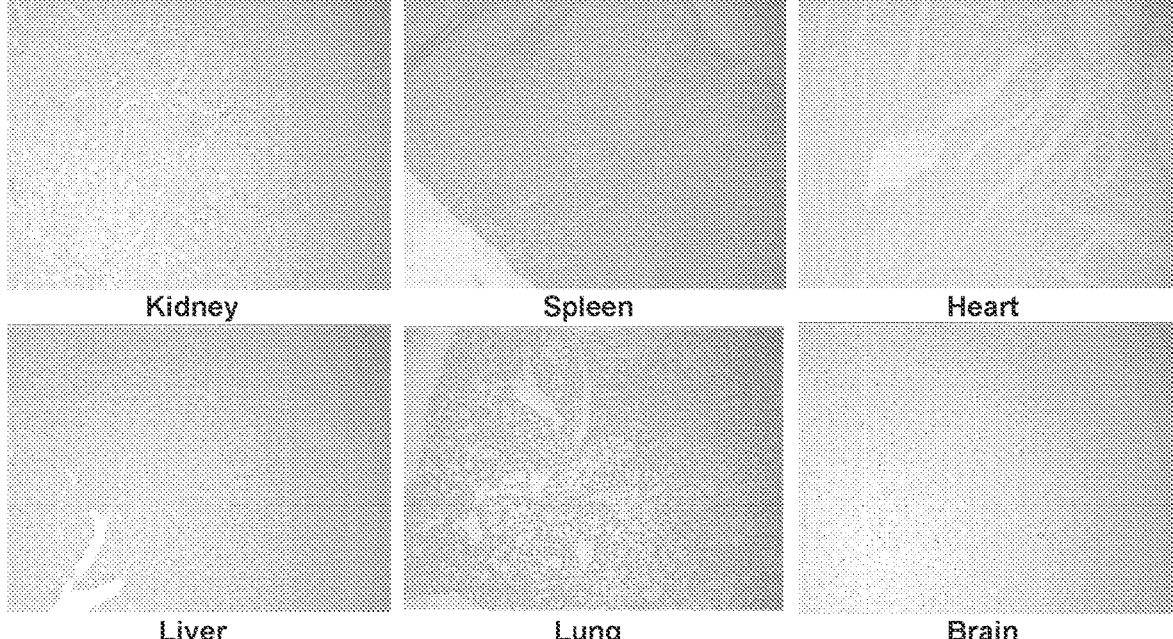
Figure 12C:
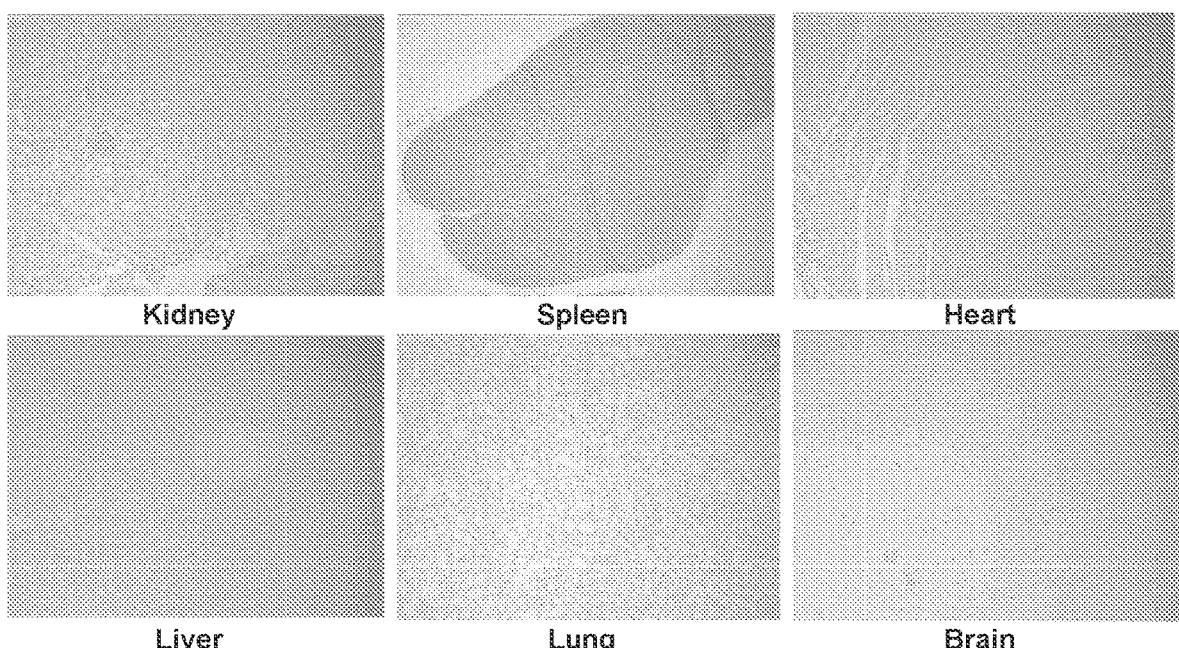
Figure 12D:
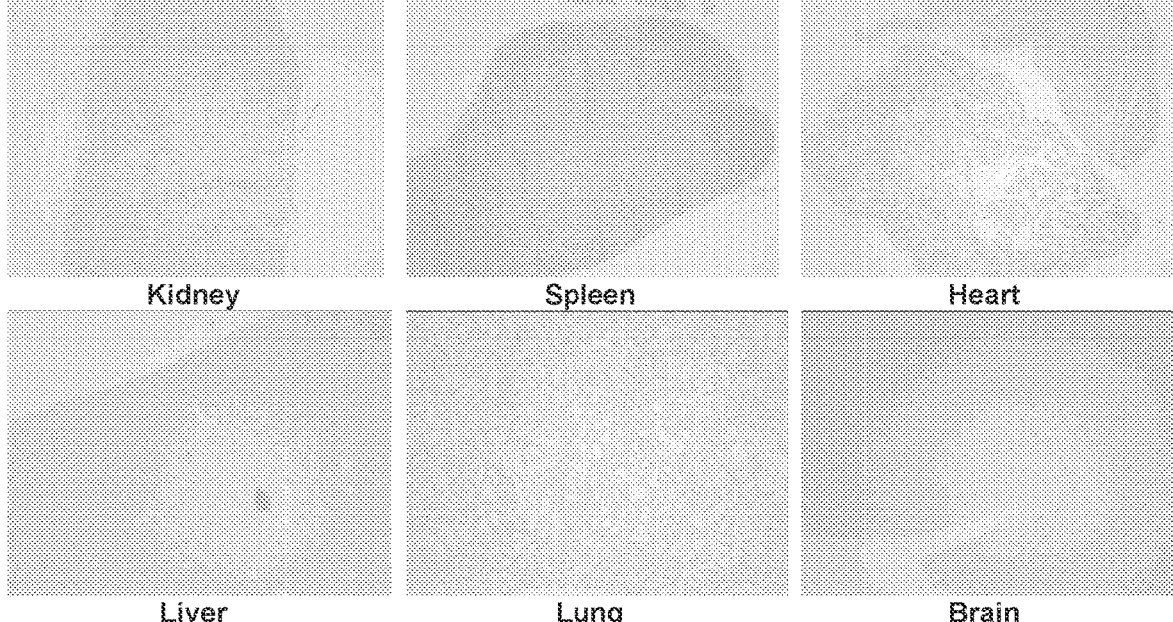

ELISAs were carried out 24 hours post-CD19 addition. The ELISA was used to detect Granzyme-B, perforin, and IL-6. Granzyme-B levels are shown in FIG. 9A-F. The results indicated a dose-dependent expression of CD19 level in Method 1 where uCAR-T cells to cancer cells ratio was 1:1. The CD19 dose-dependent expression of cytokines in Method 1 was most pronounced for SKOV3 (ovarian cancer) (FIG. 9B). CD19 Medium and CD19 Low had Granzyme-B levels that were ~59% and 46% respectively of the Granzyme-B levels in CD19 High wells. This was followed by SKBR3 (breast cancer) where CD19 Medium and CD19 Low had Granzyme-B levels that were ~93% of the Granzyme-B levels in CD19 High wells (FIG. 9A). PC3 (prostate cancer) had elevated Granzyme-B in comparison to the control cells but there was no apparent CD19 dose-dependent levels of Granzyme-B (FIG. 9C).

The results from Method 2 indicated that lowering uCAR-T cell numbers to control cytokine concentrations in samples was not a feasible method. No differences were observed between test samples and control groups. See FIG. 9D-F.

For a given cancer cell line (e.g., SKOV3) the absorbance readings from the Granzyme-B ELISA for both test and sample groups were normalized against the absorbance reading from Granzyme-B ELISA test in the CD19 test group of uCAR-T:Cancer cell=1:1

The overall cytokine levels correlated well with the results from the viability assay. SKOV3 which showed the maximum sensitivity to CD19 dose in the viability assay also showed maximum CD19 dose-dependent expression of Granzyme-B. SKBR3 which also showed sensitivity to CD19 doses in the viability assay, displayed the same trend in CD19 dose-dependent expression of Granzyme-B. But the differences in Granzyme-B levels were not as pronounced in SKBR3 cells as they were in SKOV3 cell populations. PC3 showed significant cell death only at the highest CD19 concentration. Similarly, in PC3 cells although there were higher levels of Granzyme-B in the presence of CD19, there was no clear dependence of Granzyme-B levels on CD19 dosage.

IL-6 and Perforin were also expressed in higher levels, 24 h post exposure to CD19 similar to Granzyme B for uCAR-T:Cancer cells=1:1. Overall, the ELISA results from SKOV3 indicates that it is possible to control cytokine release rates using the bridge nanoparticles and by controlling the dosage of the activator (CD19).

A bispecific bridge nanoparticle was constructed to link specific cancer cells using Herceptin and capture uCAR-T cells using anti-CD3. Conjoining the two will allow for effective disabling of the cancer cells using the properties of uCAR-T cells. This concept of a bispecific bridge nanoparticle is not limited to Herceptin and anti-CD3, but other recognition elements can be used to target structures of interest, e.g., aptamers, nanobodies, affibodies, small molecules, supramolecular assemblies, etc.

It was successfully demonstrated that off-the-shelf universal CAR-T cells can be retargeted against three different metastatic cancer cells using the bispecific bridge nanoparticles. This circumvents the obstacles that come from needing to personalize CAR-T cells to each patient and also reduces the current 21-day manufacturing timeline for CAR-T cells. It has also been demonstrated that bridge nanoparticles can enhance immunotherapy even against cancer cells such as PC3, which does not overexpress HER2 receptors that are targeted by the Herceptin on the bridge nanoparticles. These results also show that it is possible to control cytokine release rates while still causing significant cancer cell death which can possibly help to avoid cytokine release syndrome.

The bispecific bridge nanoparticles can be used to target off-the-shell uCAR-T cells to multiple types of cancer and control cytokine release from uCAR-T cells. It can also be used to retarget liposome enclosed therapeutics (e.g., gene editors CRISPR-CAS9).

The bispecific bridge nanoparticles also have the potential to recruit T-cells to cancer sites through anti-CD3 to further enhance uCAR-T cells anti-cancer activity. This treatment can be used to localize delivery of chemotherapeutics loaded in liposomes, using appropriate antigen-receptor combinations on the bridge nanoparticles and the liposomes.

Example 4

Imaging Analysis of Biodistribution, Biocompatibility and Clearance of Nanoparticles without Antibodies in Mice AF750-Bridge nanoparticles without antibodies were administered to mice through retro-orbital injection at 20 mg/kg. Animals were euthanized at 4 time points following the administration: 4 h, 8 h, 24 h, and 48 h. Organs (brain, heart, lungs, liver, spleen, kidneys, large intestine with fecal pellet) and blood were collected from the mice. The organs were imaged using an in vivo fluorescence imager with a fluorescent standard to determine nanoparticle biodistribution over time. Histology sections were stained with H&E and inflammation was scored by a pathologist.

The mice showed no distress after nanoparticle injections. The nanoparticles cleared over 48 hours. Nanoparticles were found in the fecal pellets. No statistically significant accumulation of the nanoparticles was observed in any organs. Inflammation was not detected in any of the histology sections. The Bridge nanoparticles (silica core with Au nanosphere discontinuous shells) are biocompatible, showed no non-specific accumulation and did not cause any inflammation of tissues in immunocompetent mice Balbc/j. A literature search indicated that the individual components of the bridge nanoparticles are used in medicine and have well documented dosage ranges that can be used in humans. See Table 7.

TABLE 7

In vivo Toxicity Profile of Individual Components of the Bridge Nanoparticles

| Material | Dosage | Animal Model | Admin. Mode | Toxicity | Clearance | Ref. |
|---|---|---|---|---|---|---|
| Silica 70 nm (amine modified) | 10, 20, 40 mg/kg | Mouse | Tail-vein injection | Nothing significant | Eventually through urinary and hepatobiliary route | 1-2 |
| Au nanoparticle | 2000 mg/kg | Mouse | Tail-vein injection | Highly biocompatible | Eventually through urinary and hepatobiliary route | 3-5 |
| Anti-HER2 (Herceptin) | 2 mg/kg to 8 mg/kg | Humans | Intra-venous | No unexpected toxicity | Hepatobiliary route | 6-7 |
| Anti-CD3 | 1 mg to 100 mg | humans | IV bolus or infusion | Acute dose-related leukopenia and lymphocytopenia that disappeared over time. No major side-effects | Hepatobiliary route | 8-10 |
| CD3 and HER2 bispecific antibody | 8 mg/kg | mouse | IV bolus | No unexpected toxicity | Hepatobiliary route | 11 |

1. Yu et al., *J. Control. Rel.*, 163(1): 46-54 (2012)

2. Lu et al., *Nanotechnology* 22: 055101 (2011)

3. Nebuloni et al., Academic Radiology 20(10): 1247-1255 (2013)

4. Adewale et al., *Int. J. Toxicol.* 38(5): 357-384 (2019)

5. www.nanoprobes.com/products/AuroVist-Gold-X-ray-Contrast-Agent.html

6. Kuhn and Weiner, *Immunotherapy* 8(8): 889-906 (2016)

7. Herceptin ® trastuzumab product information

8. Wiczling et al., *J. Clin. Pharmacol.* 50(5): 494-506 (2010)

9. Kuhn and Weiner, *Immunotherapy* 8(8): 889-906 (2016)

10. Urba et al., *Cancer Res.* 52: 2394-2401 (1992)

11. Yu et al., *J. Exp. Clin. Cancer Res.* 38, 355 (2019)

What is claimed is:

1. A therapeutic composition comprising:

a nanoparticle system comprising a silicon dioxide core and a plurality of gold nanospheres on the surface of the silicon dioxide core, the silicon dioxide core being selectively conjugated to one or more tumor cell targeting antibodies and the plurality of gold nanospheres being selectively conjugated to one or more T-cell targeting antibodies.

2. The composition of claim 1, wherein the tumor cell targeting antibodies bind HER2.

3. The composition of claim 1, wherein the T-cell targeting antibodies bind CD3.

4. The composition of claim 1, wherein the tumor cell targeted by the tumor cell targeting antibodies is from breast, ovarian, or prostate tissue.

5. The composition of claim 1, wherein the T-cell targeted by the T-cell targeting antibodies is a CAR-T cell.

6. The composition of claim 1, wherein the silicon dioxide core comprises a mean particle diameter ranging from about 20 nm to about 200 nm, or from about 40 nm to about 150 nm.

7. The composition of claim 1, wherein the plurality of gold nanospheres comprises about 50 gold nanospheres to about 100 gold nanospheres.

8. A method comprising:

administering the composition of claim 1 to a subject having a solid tumor.

9. The method of claim 8, wherein the tumor cell targeting antibodies bind HER2 on the surface of the tumor cell.

10. The method of claim 8, wherein the T-cell targeting antibodies bind CD3 on the surface of the T-cell.

11. The method of claim 8, wherein the solid tumor is from breast, ovarian, or prostate tissue.

12. The method of claim 8, wherein the T-cell targeted by the T-cell targeting antibodies is a CAR-T cell.

\*     \*     \*     \*     \*

SEQUENCE LISTING

```
<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: Synthetic

<400> SEQUENCE: 1

Glu Arg Pro Pro Pro Val Pro Asn Pro Asp Tyr Glu Pro Cys
1               5                   10
```